United States Patent
Kim et al.

(10) Patent No.: US 10,561,318 B2
(45) Date of Patent: Feb. 18, 2020

(54) DEVICE, SYSTEM AND METHOD FOR QUANTIFYING FLUORESCENCE AND OPTICAL PROPERTIES

(75) Inventors: Anthony Taywon Kim, Toronto (CA); Brian Campbell Wilson, Toronto (CA)

(73) Assignee: University Health Network, Toronto (CA)

( * ) Notice: Subject to any disclaimer, the term of this patent is extended or adjusted under 35 U.S.C. 154(b) by 333 days.

(21) Appl. No.: 13/575,236

(22) PCT Filed: Jan. 25, 2011

(86) PCT No.: PCT/CA2011/000090
§ 371 (c)(1),
(2), (4) Date: Sep. 20, 2012

(87) PCT Pub. No.: WO2011/088571
PCT Pub. Date: Jul. 28, 2011

(65) Prior Publication Data
US 2013/0006116 A1    Jan. 3, 2013

Related U.S. Application Data

(60) Provisional application No. 61/297,969, filed on Jan. 25, 2010.

(51) Int. Cl.
*A61B 5/00* (2006.01)
(52) U.S. Cl.
CPC .................................. *A61B 5/0059* (2013.01)
(58) Field of Classification Search
CPC ............ G01N 21/6428; G01N 21/4738; A61B 5/0059
See application file for complete search history.

(56) References Cited

U.S. PATENT DOCUMENTS

| 6,175,759 | B1 | 1/2001 | Chan et al. |
| 7,613,504 | B2 | 3/2009 | Rowe |
| 2003/0078504 | A1 | 4/2003 | Rowe |
| 2004/0044287 | A1 | 3/2004 | Lin et al. |

(Continued)

OTHER PUBLICATIONS

Georgakoudi; Sep. 2001/ vol. 40, No. 25/Applied Optics).*

(Continued)

*Primary Examiner* — Thomas J Hong
*Assistant Examiner* — Shahdeep Mohammed
(74) *Attorney, Agent, or Firm* — Nixon Peabody LLP

(57) ABSTRACT

Methods, devices and systems for quantifying fluorescence and optical properties in a turbid medium such as tissue are disclosed. One of the methods comprises: providing fluorescence emission and reflectance wavelengths detected from a target surface where each of the detected wavelengths is associated with a respective known distance between a respective excitation source giving rise to the respective detected wavelength and a detector detecting the respective detected wavelength; and calculating the optical properties based on the detected wavelengths and the respective known distances. The known distances may be predetermined to enable calculation of a desired range of values for the optical properties. The calculation of the optical properties may be based on a model of light interaction with the turbid medium where the model limits a range of calculated values for the optical properties.

24 Claims, 22 Drawing Sheets

(56) References Cited

U.S. PATENT DOCUMENTS

| | | | |
|---|---|---|---|
| 2005/0226548 | A1 | 10/2005 | Durkin et al. |
| 2006/0118742 | A1* | 6/2006 | Levenson ............ A61B 5/0059 250/559.3 |
| 2008/0076985 | A1* | 3/2008 | Matousek ............ A61B 5/0059 600/310 |
| 2008/0154126 | A1* | 6/2008 | Culver et al. ................. 600/426 |
| 2008/0194969 | A1 | 8/2008 | Werahera et al. |
| 2008/0285913 | A1 | 11/2008 | Yang et al. |
| 2009/0219526 | A1* | 9/2009 | Davisson et al. ............. 356/301 |
| 2010/0145200 | A1* | 6/2010 | Mahadevan-Jansen .................... A61B 5/0091 600/476 |
| 2012/0128264 | A1* | 5/2012 | Yazdanfar et al. ........... 382/274 |

OTHER PUBLICATIONS

Diamond et al., "Quantification of fluorophore concentration in tissue-simulating media by fluorescence measurements with a single optical fiber", Applied Optics, 42(13): 2436-2442 (2003).

Finlay et al., "Interstitial Fluorescence Spectroscopy in the Human Prostate During Motexafin Lutetium-Mediated Photodynamic Therapy", Photochemistry and Photobiology, 82: 1270-1278 (2006).

Flock et al., "Monte Carlo Modeling of Light Propagation in Highly Scattering Tissues-I: Model Predictions and Comparison with Diffusion Theory", IEEE Transactions on Biomedical Engineering, 36(12): 1162-1168 (1989).

Groehnuis et al., "Scattering and absorption of turbid materials determined from reflection measurement. 1: Theory", Applied Optics, 22(16): 2456-2462 (1983).

Lilge et al., "A solubilization technique for photosensitizer quantification in ex vivo tissue samples", Journal of Photochemistry and Photobiology B: Biology, 39: 229-235 (1997).

Muller et al., "Intrinsic fluorescence spectroscopy in turbid media: disentangling effects of scattering and absorption", Applied Optics, 40(25): 4633-4646 (2001).

Sroka et al., "Pharmacokinetics of 5-aminolevulinic-acid-induced porphyrins in tumour-bearing mice", Journal of Photochemistry and Photobiology B: Biology, 34: 13-19 (1996).

Strummer et al., "Technical Principles for Protoporphyrin-IX-Fluorescence Guided Microsurgical Resection of Malignant Glioma Tissue", Acta Neurochir, 140: 995-1000 (1998).

Weersink et al., "Noninvasive measurement of fluorophore concentration in turbid media with a simple fluorescence/ reflectance ratio technique", Applied Optics, 40(34): 6389-6395 (2001).

Wu et al., "Analytical model for extracting intrinsic fluorescence in turbid media", Applied Optics, 32(19): 3585-3595 (1993).

Supplementary European Search Report for EP 11734301 (dated Jan. 29, 2016).

* cited by examiner

|  | $\mu_{a,x}$ (cm$^{-1}$) | $\mu_{s,x}'$ (cm$^{-1}$) | $\mu_{a,m}$ (cm$^{-1}$) | $\mu_{s,m}'$ (cm$^{-1}$) |
|---|---|---|---|---|
| Phantom A | 20 | 15 | 0.02 | 8.7 |
| Phantom B | 20 | 20 | 0.02 | 11.6 |
| Phantom C | 20 | 25 | 0.02 | 14.5 |
| Phantom D | 40 | 15 | 0.04 | 8.7 |
| Phantom E | 40 | 20 | 0.04 | 11.6 |
| Phantom F | 40 | 25 | 0.04 | 14.5 |
| Phantom G | 60 | 15 | 0.06 | 8.7 |
| Phantom H | 60 | 20 | 0.06 | 11.6 |
| Phantom I | 60 | 25 | 0.06 | 14.5 |

| Pathology | Patients | # of control sites | # of tumor sites |
|---|---|---|---|
| Low-Grade Glioma | 2 | 4 | 12 |
| High-Grade Glioma | 3 | 8 | 20 |
| Meningioma | 6 | 13 | 20 |
| Lung metastasis | 3 | 12 | 12 |

FIG. 17

| | [PpIX] (μg/mL) Normal tissue | [PpIX] (μg/mL) Tumor tissue | [PpIX] T/N ratio (based on averages) |
|---|---|---|---|
| All tumors | 0.008 ± 0.018 | 1.27 ± 3.78 | 155 |
| LGGs | 0.004 ± 0.002 | 0.98 ± 3.22 | 266 |
| HGGs | 0.007 ± 0.007 | 1.48 ± 5.56 | 225 |
| Meningioma | 0.014 ± 0.028 | 1.59 ± 2.89 | 116 |
| Metastasis | 0.003 ± 0.005 | 0.66 ± 0.96 | 222 |

FIG. 21

| Diagnostic variable | Using in vivo glioma data | | Using in vivo all-tumors data | |
|---|---|---|---|---|
| | $p$ | $h$ ($h=1$ if $p<0.05$) | $p$ | $h$ ($h=1$ if $p<0.05$) |
| [PpIX] (μg/mL) | <0.001 | 1 | <0.001 | 1 |
| AF ($\lambda=600$ nm) (nm$^{-1}$·cm$^{-1}$) | 0.346 | 0 | <0.001 | 1 |
| AF ($\lambda=635$ nm) (nm$^{-1}$·cm$^{-1}$) | 0.974 | 0 | 0.010 | 1 |
| AF ($\lambda=650$ nm) (nm$^{-1}$·cm$^{-1}$) | 0.792 | 0 | 0.064 | 0 |
| AF ($\lambda=700$ nm) (nm$^{-1}$·cm$^{-1}$) | 0.445 | 0 | 0.717 | 0 |
| R ($r=260$ μm, $\lambda=575$ nm) (cm$^{-2}$) | <0.001 | 1 | <0.001 | 1 |
| R ($r=260$ μm, $\lambda=600$ nm) (cm$^{-2}$) | 0.039 | 1 | <0.001 | 1 |
| R ($r=520$ μm, $\lambda=575$ nm) (cm$^{-2}$) | <0.001 | 1 | <0.001 | 1 |
| R ($r=520$ μm, $\lambda=600$ nm) (cm$^{-2}$) | 0.003 | 1 | <0.001 | 1 |
| $\mu_a$ ($\lambda=575$ nm) (cm$^{-1}$) | 0.002 | 1 | 0.060 | 0 |
| $\mu_a$ ($\lambda=600$ nm) (cm$^{-1}$) | 0.045 | 1 | 0.152 | 0 |
| $\mu_s'$ ($\lambda=575$ nm) (cm$^{-1}$) | 0.251 | 0 | <0.001 | 1 |
| $\mu_s'$ ($\lambda=600$ nm) (cm$^{-1}$) | 0.245 | 0 | 0.014 | 1 |
| StO2 | 0.002 | 1 | 0.288 | 0 |
| $f_{Hb}$ (g/L) | 0.002 | 1 | 0.070 | 0 |

FIG. 22

|  | ROC a.u.c. (s.e.) | Sensitivity (%) | Specificity (%) |
|---|---|---|---|
| Surgeon's visible fluorescence score | 0.734 (0.029) | 58.6 | 78.0 |
| Raw fluorescence spectroscopy @ 635 nm | 0.571 (0.035) | 51.6 | 84.8 |
| [PpIX] (µg/mL) | 0.880 (0.019) | 79.7 | 86.9 |
| Linear discriminant analysis | 0.922 (0.022) | 87.1 | 89.1 |

FIG. 25

|  | ROC a.u.c. (s.e.) | Sensitivity (%) | Specificity (%) |
|---|---|---|---|
| Surgeon's visible fluorescence score | 0.775 (0.051) | 62.6 | 83.1 |
| Raw fluorescence spectroscopy @ 635 nm | 0.577 (0.052) | 55.0 | 98.3 |
| [PpIX] (µg/mL) | 0.945 (0.022) | 88.3 | 93.3 |
| Linear discriminant analysis | 0.967 (0.016) | 92.8 | 96.2 |

FIG. 26

|  | ROC a.u.c. (s.e.) | Sensitivity (%) | Specificity (%) |
|---|---|---|---|
| Surgeon's visible fluorescence score | 0.542 (0.095) | 50.2 | 54.3 |
| Raw fluorescence spectroscopy @ 635 nm | 0.247 (0.049) | 22.2 | 73.3 |
| [PpIX] (µg/mL) | 0.651 (0.059) | 47.2 | 93.3 |
| Linear discriminant analysis | 0.800 (0.068) | 77.4 | 89.0 |

FIG. 27

|  | ROC a.u.c. (s.e.) | Sensitivity (%) | Specificity (%) |
|---|---|---|---|
| Surgeon's visible fluorescence score | 0.750 (0.062) | 60.0 | 80.0 |
| Raw fluorescence spectroscopy @ 635 nm | 0.664 (0.070) | 66.7 | 95.8 |
| [PpIX] (µg/mL) | 0.984 (0.016) | 91.7 | 95.8 |
| Linear discriminant analysis | 0.978 (0.050) | 95.9 | 97.3 |

FIG. 28

| | ROC a.u.c. (s.e.) | Sensitivity (%) | Specificity (%) |
|---|---|---|---|
| Surgeon's visible fluorescence score | 0.800 (0.043) | 65.5 | 86.2 |
| Raw fluorescence spectroscopy @ 635 nm | 0.694 (0.053) | 58.3 | 100.0 |
| [PpIX] (µg/mL) | 0.898 (0.031) | 78.3 | 87.2 |
| Linear discriminant analysis | 0.947 (0.057) | 91.9 | 92.2 |

FIG. 29

DEVICE, SYSTEM AND METHOD FOR QUANTIFYING FLUORESCENCE AND OPTICAL PROPERTIES

CROSS REFERENCE TO RELATED APPLICATIONS

This application is a 35 U.S.C. § 371 National Phase Entry Application of International Application No. PCT/CA2011/000090, filed Jan. 25, 2011, which designates the United States, and which claims benefit under 35 U.S.C. § 119(e) of the U.S. provisional application No. 61/297,969, filed on Jan. 25, 2010, the contents of which are herein incorporated by reference in their entirety.

TECHNICAL FIELD

The present disclosure relates to devices for quantifying fluorescence and optical properties. In particular, the present disclosure relates to probe devices and methods for quantifying fluorescence in an optically turbid medium, such as tissue, using optical properties measurements.

BACKGROUND

The present disclosure is related to fluorescence imaging and spectroscopy, in particular the use of fluorescence to detect and/or treat cancer by marking tumor cells with an appropriate fluorescing agent. One difficulty in using fluorescence for medical diagnostics and therapeutics is quantifying the fluorescence in tissue. Fluorescence signals are strongly affected by variations in the tissue absorption and transport scattering properties (i.e. tissue optical properties), whereas often the objective is to quantify the fluorescence based on fluorophore concentration alone.

Fluorescence measurement is of interest for applications such as photosensitizer dosimetry during photodynamic therapy (Finlay et al. 2006), fluorescence image-guided surgery (Stummer et al. 1998), detection of cancerous or dysplastic lesions (Muller et al., 2001) and in time kinetics studies of fluorescing drugs (Sroka et al. 1996). The shape and intensity of the fluorescence spectrum contain useful information on the identity and abundance of fluorophores in tissue. However, accuracy of quantitative fluorescence measurement is complicated by the distorting effects of light absorption and scattering by the tissue and the variations in measurement geometry (e.g. detector-to-tissue surface distance). Untangling these confounding effects is important for quantitative analysis of fluorescence.

Some methods have been developed in an attempt to diminish these distorting effects to better utilize fluorescence information. Many of these techniques use a diffuse reflectance signal to correct the fluorescence signal from optical properties variation. Wu and coworkers have developed a fluorescence photon migration model to produce a relation with the diffuse reflectance that can be exploited to extract the quantitative fluorescence in tissue (Wu et al. 1993). On a different tack, a single optical fiber may be used for both source and collection, the concept being that detectable fluorescence events occur so close to the fiberoptic tip that absorption and scattering effects are minimal, analogous to how these effects are minimal for very thin tissue sections (Diamond et al. 2003).

Empirical methods with similar themes have also been developed. The single fiber method was used in conjunction with an empirically-derived correction factor dependent on the optical properties at the emission wavelength to further compensate for high tissue attenuation in the prostate during PDT studies (Finlay et al. 2006). A fluorescence/reflectance ratio has been used to quantify fluorophore concentration, but with the fluorescence and reflectance measured at different source-collector distances (Weersink et al. 2001). In all of the above methods, the excitation source operates in the region of low tissue absorption, which invalidates their use in the UV-blue-green end of the spectrum (i.e. approximately from 350-575 nm), where a very large subset of fluorophores have fluorescence absorption maxima, such as porphyrins, background autofluorescence and a multitude of artificial fluorescent dyes.

Ex vivo extraction techniques have also been developed that are based on homogenizing the tissue and diluting the analyte to the point that effects due to optical scattering and absorption are negligible (Lilge et al. 1997). These procedures are relatively time-consuming and open to error due to tissue handling or cryofreezing for post-processing. It would be useful to provide an in situ fluorometric approach that has applicability to a wide variety of fluorophores and tissues.

SUMMARY

The present disclosure describes a device for quantifying fluorescence and optical properties in a turbid medium, such as tissue. In particular, the device may be in the form of a fiberoptic probe for use in fluorometric applications in tissue. The present disclosure also describes an associated system for controlling optical signals to and from the probe and algorithms to quantify optical parameters from the probe measurements. The disclosed device may be used as an in vivo instrument to quantify fluorescence in tissue. The device and associated systems and methods may compensate for the effects of tissue optical property variation on the perceived fluorescence.

In some examples, the fiberoptic probe generally has a handle attached to a hypodermic needle-like probe that contacts tissue, which may be flat and includes a linear array of fiberoptics at the tip. Alternatively, the tip may be configured to have an angle or taper such that it may more easily push through tissue, for example for interstitial measurement, similar to a hypodermic needlepoint. A series of excitation light sources are routed through the probe tip via a source fiberoptic and the resulting reflectance and/or fluorescence spectra are measured at a distance through a detector fiber. In this way, measurements of the tissue fluorescence and white light reflectance (reflectance may be taken at varying source-collector fiberoptic distances) can be made. Applying an appropriate model of light interaction with tissue, the quantitative fluorescence, absorption and transport scattering properties ($\mu_a$ and $\mu_s'$) of the tissue can be determined, as well as other physiological metrics such as tissue oxygenation and hemoglobin concentration.

In some examples, the device includes: a handheld probe culminating in a narrow tip that contacts the tissue; fiberoptics bundled into the probe tip and probe handle and leading to a control system; the fiberoptics at the tip arranged in a linear array. The device may be used with: a control system that routes optical signals to and from the probe handle; a computer that is connected to the control system. The device may be used with algorithms to compute the optical properties and derive the quantitative fluorescence. The system may provide the software on the computer to handle the algorithm computation, data acquisition and control; and a user interface to control the settings of the data acquisition.

The disclosed device, system and method may be used to extract the quantitative fluorescence spectrum (i.e. the fluorescence spectrum corrected for optical properties effects), and consequently fluorophore concentration, using a fiberoptic probe that comes into contact with or is buried interstitially within the tissue. The optical properties, diffuse reflectance spectrum and measured fluorescence spectrum (i.e. the raw, uncorrected fluorescence measurement that is distorted by optical properties effects) are inputs to the model. Since the tissue optical properties need to be known, a method to extract these is also described, that may be referred to as spectrally-constrained diffuse reflectance.

In some aspects, there is provided an optical probe for quantifying fluorescence and optical properties in tissue, the probe comprising: a probe body and a probe tip at a distal end of the probe body, the probe tip being configured to substantially contact a target surface; at least one detector at the probe tip for detecting fluorescence emission or reflectance wavelengths from the target surface; at least one fluorescence excitation source at the probe tip for providing fluorescence excitation light to the target surface, each one of the at least one fluorescence excitation source being at a known distance from each one of the at least one detector; at least two broadband sources at the probe tip for providing broadband wavelengths to the target surface, each one of the at least two broadband sources being at a known distance from each one of the at least one detector; wherein the device is configured to communicate signals from the at least one detector representing the detected wavelengths to a processing device.

In some aspects, there is provided a method for quantifying optical properties in a turbid medium, the method comprising: providing fluorescence emission and reflectance wavelengths detected from a target surface, each of the detected wavelengths being associated with a respective known distance between a respective excitation source giving rise to the respective detected wavelength and a detector detecting the respective detected wavelength, the known distances being predetermined to enable calculation of a desired range of values for the optical properties; and calculating the optical properties based on the detected wavelengths and the respective known distances, and based on a model of light interaction with the turbid medium, the model limiting a range of calculated values for the optical properties.

In some aspects, there is provided a method for quantifying fluorescence in a turbid medium, the method comprising: providing fluorescence emission and reflectance wavelengths detected from a target surface, each of the detected wavelengths being associated with a respective known distance between a respective excitation source giving rise to the respective detected wavelength and a detector detecting the respective detected wavelength, the known distances being predetermined to correspond to a desired range of values for the optical properties; providing quantified optical properties corresponding to the detected wavelengths; and calculating the fluorescence based on the detected wavelengths and the corresponding optical properties, based on known relationships between the detected fluorescence emission wavelengths and the detected reflectance wavelengths arising from the known distances, and based on a model of light interaction with the turbid medium, the model limiting a range of calculated values for the optical properties. In some examples, the method for quantifying fluorescence may also include the method for quantifying optical properties described above.

In some aspects, there is provided a system for quantifying optical properties in tissue, the system comprising: the probe described above; a plurality of light sources for providing fluorescence excitation and broadband wavelengths to the fluorescence excitation source and broadband sources; a spectrometer for measuring wavelengths detected by the detector; and a controller for controlling fluorescence emission and detection by the sources and the detector; wherein the system is in communication with a processing device configured for calculating at least one optical property based on the measured wavelengths.

BRIEF DESCRIPTION OF THE DRAWINGS

FIG. 17 is a table showing baseline characteristics for patients in an example study of an example system and method for quantifying optical properties;

FIG. 21 is a table showing comparisons of example PpIX concentration levels from an example study of an example system and method for quantifying optical properties;

FIG. 22 is a table showing example diagnostic variables tested in an example study of an example system and method for quantifying optical properties;

FIGS. 25-29 are tables of example data for diagnostic variables tested in an example study of an example system and method for quantifying optical properties.

DETAILED DESCRIPTION

The present disclosure describes a device, system and method that may be used for recovering the quantitative fluorescence, individual fluorophore concentrations, and/or other optically-determined physiological metrics (e.g., in the case of tissue, the tissue oxygenation, hemoglobin concentration, etc. may be recovered). Any measureable tissue fluorescence may be significantly affected by the measurement geometry and tissue optical properties. For example, fluorescence image intensity (in epi-illumination mode) varies with camera-to-tissue distance approximately according to an inverse law. An increased blood volume significantly attenuates fluorescence intensity due to the high absorption of hemoglobin. Attempts to quantify the fluorescence without taking into account these factors may lead to incorrect interpretation.

The disclosed device, system and method may help reduce, minimize or eliminate the issue of varying measurement geometry by fixing the source and detector geometry (e.g., as mediated with fiberoptics embedded in a cylindrical probe head) and by making contact with the tissue during measurement. As well, measurement of optical properties in combination with a novel fluorescence model and algorithm may be used to remove the distorting effects of the tissue optical properties.

The present disclosure describes a combination of the "hardware" equipment (e.g., fiberoptic probe, control system and computing hardware) required to produce the spectroscopic measurements and the "software" algorithms to process the raw data to reconstruct the quantitative fluorescence spectrum, fluorophore concentration(s), optical properties and/or physiological metrics such as tissue oxygenation and hemoglobin concentration in the case of tissue. The software part may be further divided into the optical properties calculation part and the quantitative fluorescence calculation part. The result from the optical properties calculation is used in the quantitative fluorescence part; however, any suitable method of obtaining optical properties may be used in the quantitative fluorescence part. Thus, although the two are discussed together, the quantitative fluorescence calculation may be performed independent of the described optical properties calculation, even though the result of the optical properties calculation is used in the quantitative fluorescence calculation. The following description discusses the hardware and software parts separately; however, both parts may be used together.

Figure 1:
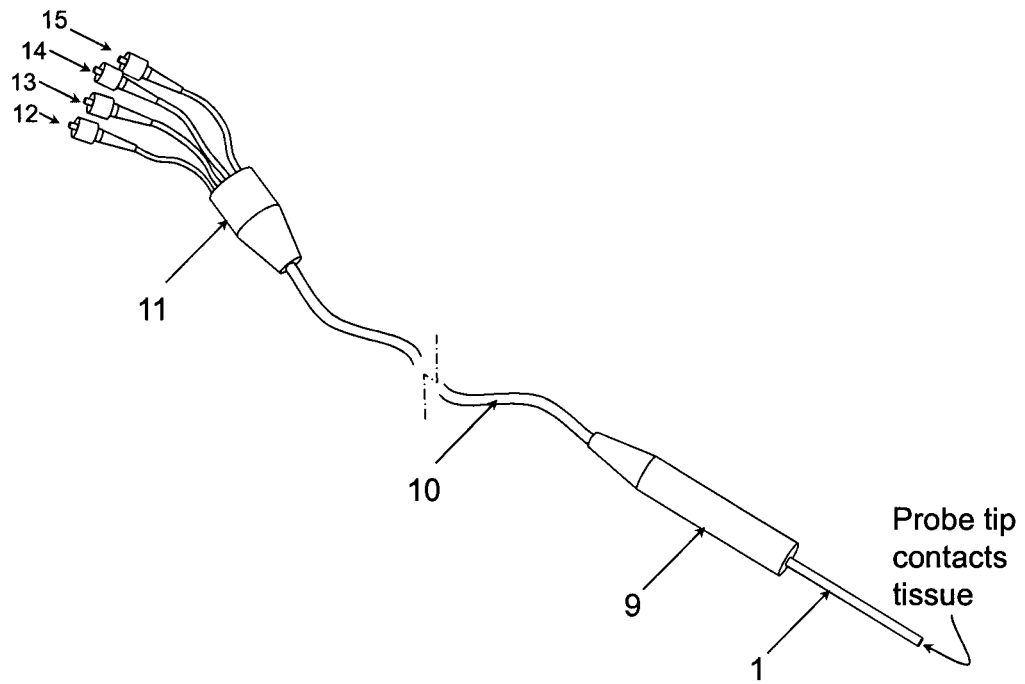
FIG. 1 is a schematic of an example device for quantifying fluorescence and optical properties.
Figure 3:
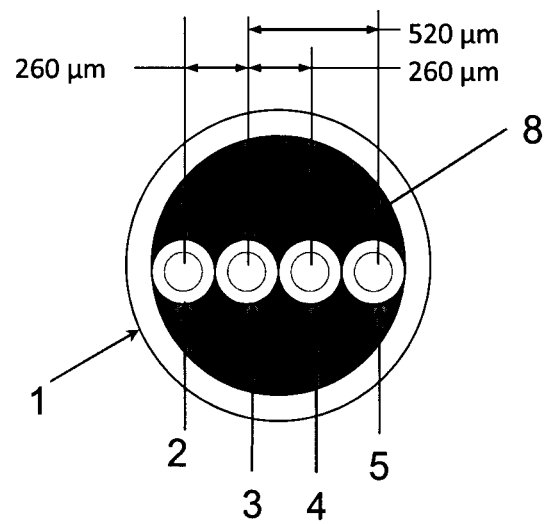
FIG. 3 is an end-on view of an example probe tip suitable for the example device of FIG. 1 or FIG. 2.
Figure 4:
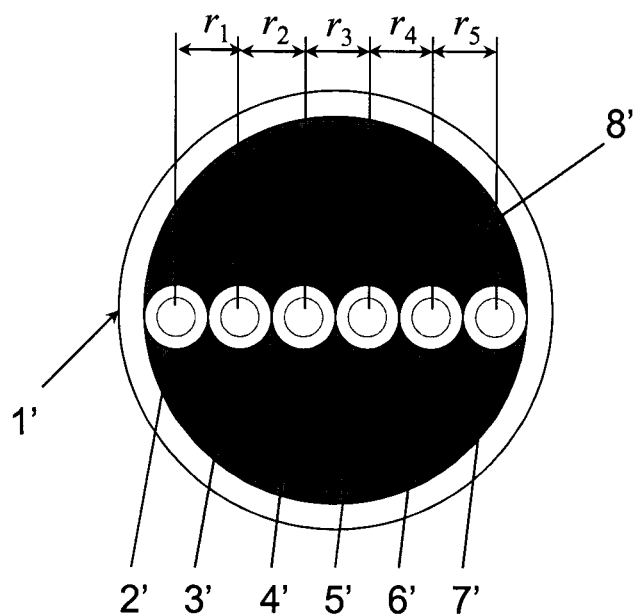
FIG. 4 is an end-on view of another example probe tip suitable for the example device of FIG. 1 or FIG. 2.

The following is a description of an example of the hardware portion. FIG. 1 illustrates an example of the device, in this case a portable fiberoptic probe. In this example, the handle 9 is connected to the probe barrel 1 on one end and the fiberoptic lead 10 leading back to the control system (not shown) where the optical signals are received. The tip of probe barrel 1 is the part that actually contacts the tissue site of interest. Examples of suitable tip geometries are shown in FIG. 3 and FIG. 4. The fiberoptic lead 10 includes, in this example configuration, four separate optical fibers, which are split apart from the main lead into four separate leads by part 11. The four separate leads terminate into fiberoptic connectors 12, 13, 14 and 15. The fiberoptic lead 10 connects the probe via connectors 12,13,14 and 15 to the control system (see FIG. 5).

Figure 2:
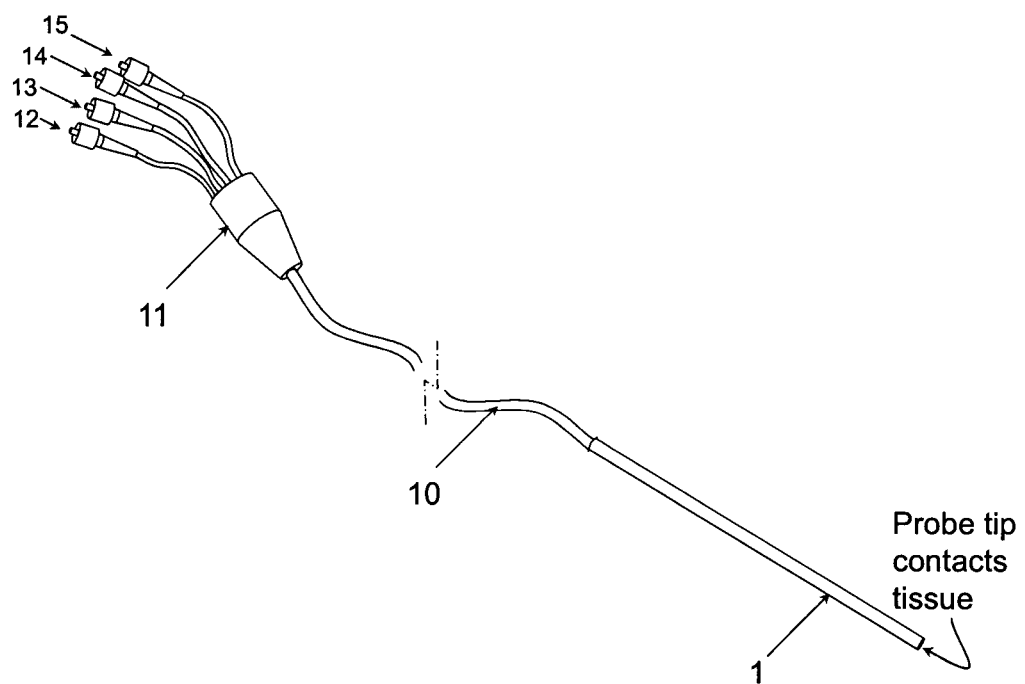
FIG. 2 is a schematic of another example device for quantifying fluorescence and optical properties.

The probe may also be catheterizable, as shown in the example device of FIG. 2. The example shown in FIG. 2 is similar to that of FIG. 1, however in FIG. 2, the probe barrel 1 is connected directly to the fiberoptic lead 10 to enable catheterization. Other such modifications may be made to the device to accommodate its use in various procedures.

In some examples, the probe tip geometry can take the form shown in FIG. 3. FIG. 3 is an end-on view of an example of the probe tip. The fibers are aligned in a linear array with varying distances from each other. In this example configuration, adjacent fibers are 260 µm apart. Probe barrel 1 has the optical fibers built into it, for example held in place with epoxy 8 or any other suitable fixative, such that their geometry with respect to each other is well-defined and relatively unchangeable. Fibers 2-5 in this case are connected to fiberoptic connectors 12-15 (see FIG. 1). The probe tip may be ground flat and polished in order to maximize signal from the probe tip.

The probe tip may have more than four fibers, such as that as shown in the example tip of FIG. 4. In this example, six fibers are shown, although more or less fibers may be used. The fibers are located at known distances from each other. One source-collector pair is used to measure the tissue fluorescence spectrum (for example, in the example probe tip of FIG. 4, this may be fiber 2' as the fluorescence excitation source and fiber 3' as the detector). The other fibers are used to measure the diffuse reflectance spectrum at different fiberoptic separation distances (for example, in FIG. 4, the detector fiber 3' measures the diffuse reflectance spectrum at different distances as white light is sequentially sent through fibers 4', 5', 6' and 7'). Although in the examples shown, the source and detection fibers are arranged in a linear manner, other fiber configurations may be possible. For example, the fibers may be arranged in a circular, staggered or random configuration, as long as their relative distances r are defined. In the example method and model described below, it may be useful to have at least one white light source fiber at the same distance from the detector fiber as at least one fluorescence excitation source fiber. There may be more than one fluorescence excitation source fiber provided, with possibly different fluorescence excitation wavelengths for different fluorescence excitation source fibers. In some examples, it may be useful to have all fluorescence excitation source fibers the same distance away from the detector. The use of different excitation wavelengths may allow for excitation of a variety of fluorophores. For example, one way to implement multiple fluorescence excitation source fibers into the example shown in FIG. 3 may be to add fluorescence excitation source fibers 260 µm above and beneath the detector fiber 3.

The use of multiple fiberoptic distances for measuring the diffuse reflectance is related to techniques in measuring the tissue optical properties (recall that the tissue optical properties need to be estimated to feed into the quantitative fluorescence algorithm). Spectrally-constrained diffuse reflectance methods have been developed that allow the use of a single fiberoptic source-collector pair (for example, see FIG. 8). The source fiber delivers broadband or white light and the diffuse reflectance spectrum is detected by the collector fiber located at a distance, r. Since there is only one reflectance measurement per wavelength, $\lambda$, solving for $\mu_a$ and $\mu_s'$ relies upon spectral constraints, i.e. applying a priori knowledge of the shapes of $\mu_a(\lambda)$ and $\mu_s'(\lambda)$ in a forward model, which can then be used to solve for the absolute coefficient values. A challenge with the spectrally-constrained diffuse reflectance method is the relatively limited dynamic range of $\mu_a$ and $\mu_s'$ that can be measured with a single source-collector distance. Therefore, one of the purposes of using multiple source-collector distances for measuring the diffuse reflectance is to span a large dynamic range of optical properties. Since each distance spans a unique range over which $\mu_a$ and $\mu_s'$ can be measured, overlap of the reflectance measurements at multiple distances may help to extend the dynamic range beyond that of each distance separately.

Figure 10:
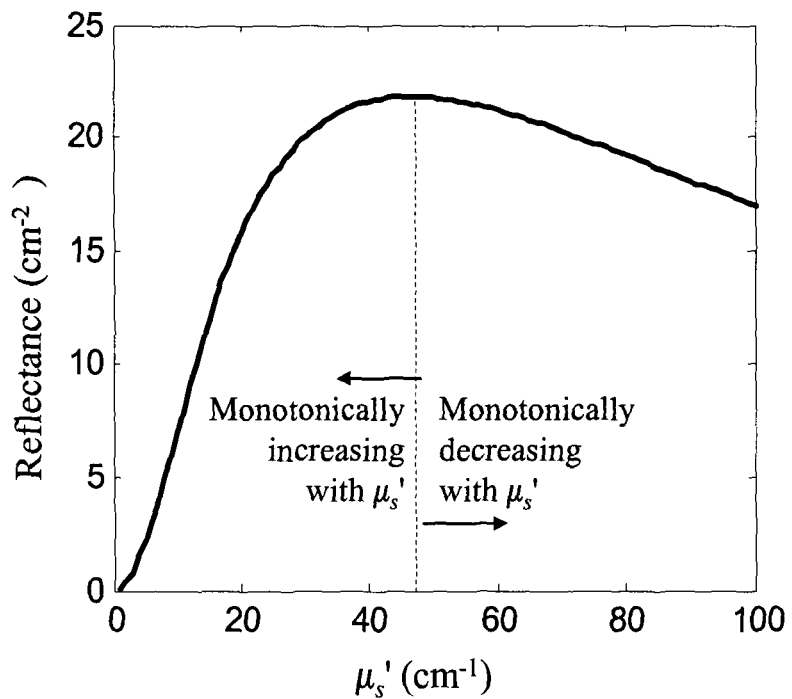
FIG. 10 shows a graph of reflectance versus $\mu_s'$ for an example fiberoptic distance of 500 μm.

The way that reflectance behaves with increasing reduced scattering coefficient, $\mu_s'$, is to increase with increasing $\mu_s'$, peak, and then decrease. An example of this is shown in FIG. 10, which is an example graph of reflectance versus $\mu_s'$ for a fiberoptic distance of 500 µm. The peak is indicated as a cut-off point for the "usefulness" of the reflectance for estimating the optical properties, since only the part which is monotonically increasing or the part that is monotonically decreasing can be used, but not both. It has been found that the monotonically increasing part is more sensitive to changes in $\mu_s'$, so this part is used for optical properties measurement in the examples described. However, it should be understood that the monotonically decreasing part may also be used. The reflectance peak of FIG. 10 is at relatively high $\mu_s'$ for small fiberoptic distance, r; hence, close fiberoptic distances (in this example, r<2 mm) are used to span a large dynamic range of $\mu_s'$.

Figure 11:
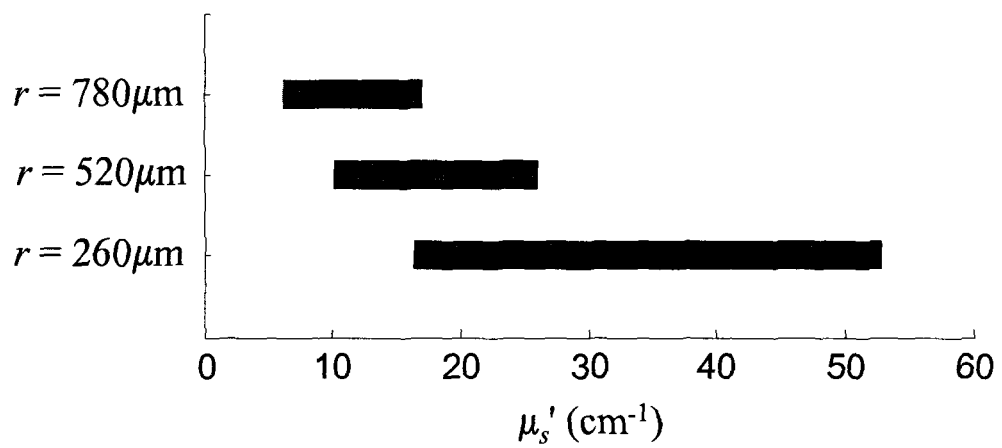
FIG. 11 shows a bar graph for three example fiberoptic distances (r=260, 520 and 780 μm) and their range of validity according to an example model for quantifying optical properties.

In the disclosed device, there are multiple optical fibers for measuring the diffuse reflectance in order to span a large range of tissue optical properties. Since a diffusion theory model is used for optical properties extraction (described below), there is a lower bound of validity of $\mu_s'$ for a given r such that diffusion theory is valid. As well, if the monotonically increasing part (with respect to $\mu_s'$) is being used then the reflectance peak (see FIG. 10) represents an upper bound for a given r. Therefore, different r distances have different dynamic ranges for optical properties measurement. For example, in the case of r=260, 520 and 780 µm, these dynamic ranges are shown in FIG. 11. FIG. 11 shows a bar graph for three fiberoptic distances (r=260, 520 and 780 µm) and their range of validity according to the reduced scattering coefficient, $\mu_s'$. The lower bound is due to the diffusion theory model breaking down at low $\mu_s'$; the upper bound is due to the reflectance peak. This figure shows the need for multiple fiberoptic distances, r, to span a large overall dynamic range of optical properties. The technique of spectrally constrained diffuse reflectance using multiple r to expand the dynamic range of optical properties measurement may differ from conventional methods.

An alternative purpose to having multiple source-collector distances for measuring tissue optical properties is to use a technique called spatially-resolved diffuse reflectance. Essentially, the reflectance measurements at multiple r can constrain the solution such that $\mu_a$ and $\mu_s'$ can be solved for in a non-linear least squares solution. This solution may have some drawbacks, including, for example: relatively slower acquisition times and larger r values, which may necessitate bulkier probe head diameters; and a less robust solution that may lead to spurious results in a dynamically changing biological environment (e.g. breathing and pulsatile blood flow). Spatially-resolved diffuse reflectance is, however, still a viable technique for extracting tissue optical properties for the purpose of inputting into the quantitative fluorescence algorithm.

In operation, the probe sequentially sends fluorescence excitation light and broadband light (for each r distance) into the tissue to obtain the fluorescence and diffuse reflectance spectra, respectively. The fluorescence spectrum depends on five main parameters, the absorption and transport scattering coefficients at the excitation wavelength, $\mu_{a,x}$ and $\mu_{s,x}'$, and the emission wavelength, $\mu_{a,m}$ and $\mu_{s,m}'$, and fluorophore content. In this disclosure, the x and m suffices are used to denote excitation and emission, respectively. The reflectance spectrum depends on the wavelength-dependent absorption and scattering coefficients, $\mu_a(\lambda)$ and $\mu_s'(\lambda)$. Based on a diffusion theory model of light transport in tissue, all of these quantities can be calculated from the fluorescence and reflectance measurements. As well as fluorescence quantification being achieved, many other useful parameters can be calculated from the data, such as tissue oxygenation, hemoglobin concentration and a metric of the abundance of optical scatterers in tissue such as cells, organelles and the extracellular matrix.

Figure 5:
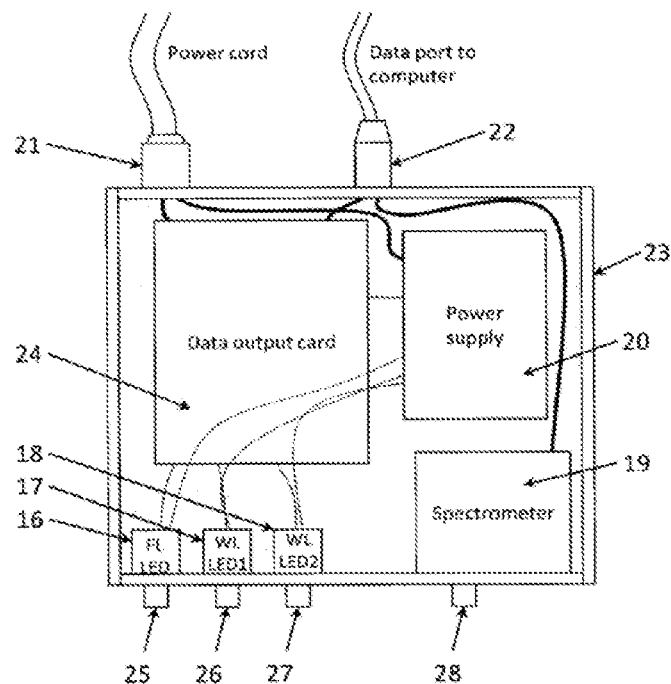
FIG. 5 is a schematic of an example system suitable for use with the example device of FIG. 1 or FIG. 2.

FIG. 5 shows a schematic of an example system suitable for use with the device described above. This example control system may be used to control optical signals flowing into and out of the example probe. A data output card 24 communicates with and is controlled by a processing device, such as an external computer (not shown). The system also includes a spectrometer 19 that communicates with the processing device. The data output card 24 controls multiple light-emitting-diodes (LEDs) 16, 17 and 18 that provide the excitation light for the fluorescence and white light reflectance spectral measurements. The data output card 24 communicates to a processing device (e.g., an example control computer) for data acquisition and control via a data output port 22. Fiberoptic connector ports 25, 26, 27 and 28 are used to connect the fiberoptic probe to the control system. The detector fiber (for example, in FIG. 3 and FIG. 4 the fiber in the probe tip is 3 and 3', respectively) is plugged into the spectrometer 19. Alternatively, a detector with an appropriate emission filter may be used for single-wavelength detection. Another possibility for detection would be a charge-coupled device (CCD) in combination with a diffraction grating or prism. In all detection configurations, there may be the option to insert a longpass filter in front of the detector to reject the fluorescence excitation. The fluorescence excitation fiber (for example, in FIG. 3 and FIG. 4 this is fiber 2 and 2') is connected to a narrow wavelength band light source, such as an LED 16 as shown (in some examples, a laser or filtered white light source may also be used), through port 25. Additional light sources 17, 18 (for example, LEDs, halogen lamps or other lamps) for the diffuse reflectance measurements send light sequentially through ports 26 and 27. A power supply 20 supplies appropriate voltage and current to all devices (e.g., LEDs and any other electronics) as necessary. An enclosure 23 contains all electrical devices in such a manner that external devices (e.g., the fiberoptic probe and the computer) may be connected to it easily, and that the enclosure is made electrically safe. The enclosure 23 may provide a port for the external electrical supply 21 and a data port 22 (e.g., to connect to a computer).

Although the example system has been described with certain components, variations may be possible. The system may have more LEDs than those shown. The system may be portable (e.g., the system may include a portable power source such as a battery, and may include an embedded microprocessor rather than communicating with an external processing device). Rather than a data output card in communication with an external computer, the system may include a processor for performing the functions of these components, for example as described above. In some embodiments, the system may communicate wirelessly with an external processing device rather than through data ports. The system may be adapted or configured to carry out a method for quantifying optical properties, for example by carrying out calculations based on the model described below. In other examples, the system may communicate with an external processing device to carry out such calculations.

Example Device and System

An example of the above-described device and system is described below. The example is based on the examples shown in FIG. 1, FIG. 3 and FIG. 5. The example may be suitable for pre-clinical and/or clinical evaluation of quantitative fluorescence, for example for delineation of brain tumors during resection surgery. A photograph of the example fiberoptic probe is shown next to a 28 mm diameter Canadian two-dollar coin (for scale) in FIG. 6a. In the example shown, the probe includes a fiberoptic lead, in this case a 3 m long fiberoptic lead. In this example, a linear array of four optical fibers (ThorLabs, Newton, N.J., USA), spaced apart every 260 μm, were epoxied into an 18 Ga hypodermic needle tube. The silica core of the fiber was 200 μm, with a numerical aperture of 0.22. The hypodermic needle part was affixed to a stainless steel handle, with the four fibers extending 3 m to SMA 905 fiberoptic connectors.

Figure 6:
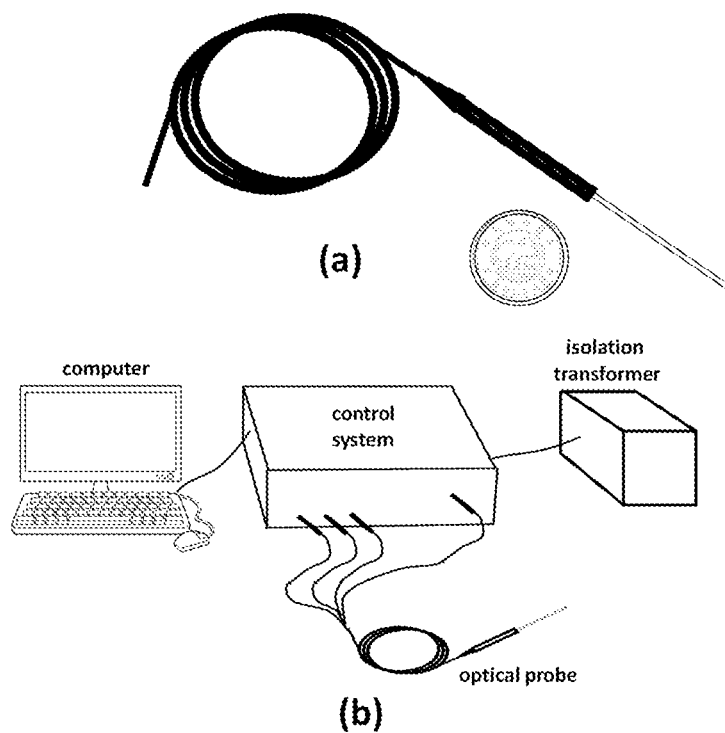
FIG. 6a and FIG. 6b show photographs of an example device and an example system for quantifying fluorescence and optical properties.

The example system is shown in FIG. 6b. In this example, the system includes the probe, and a control system, in communication with an external processing device, in this case a data acquisition computer. The system may also include an isolation transformer, as shown, for additional electrical isolation, which may be useful when the system is to be used in the operating theatre. The control system directs the flow of optical signals into and out of the probe handle. The white light sources for the diffuse reflectance measurements and the source for fluorescence excitation (in this example, at around 405 nm) in this example are LEDs (LEDengin, Santa Clara, Calif., USA), controlled by computer via a data output card (Measurement Computing, Norton, Mass., USA). The fluorescence LED was filtered with a 550 nm shortpass filter (Edmund Optics, Barrington, N.J., USA). The spectrometer was a USB2000+ model (Ocean Optics, Dunedin, Fla., USA). In other examples, the fluorescence excitation wavelength may be in the range of about 350 nm to about 600 nm, for example 500 nm to about 600 nm or 380 nm to about 420 nm, although other ranges may also be used, including wavelengths greater than 600 nm and wavelengths less than 350 nm. The fluorescence excitation wavelength may be selected based on known characteristics of the excitation target, which may be, for example, a tissue target or a fluorophore. For example, when the excitation target is a tissue having a significant hemoglobin content, the excitation wavelength may be selected to be no greater than about 600 nm since hemoglobin has greater absorption at wavelengths less than 600 nm; for other excitation tissue or non-tissue targets which absorb wavelengths in different ranges, other excitation wavelength ranges may be used.

A data acquisition computer (e.g., a desktop computer or a laptop computer) may be used to control the LED signals and spectrometer acquisition. The computer may include software for carrying out data acquisition using the system. In other examples, the system may itself be configured to execute such software, without communicating with an external processing device. In this example, the program acquired the following sequence of measurements:

1. White light reflectance spectrum @ r=260 μm
2. White light reflectance spectrum @ r=520 μm
3. Fluorescence spectrum (405 nm excitation) @ r=260 μm
4. Background signal (no light through probe)

In this example, a measurement sequence takes ~0.5 seconds. These measurements may be used in a model for quantifying optical properties, as discussed below. In this example, the white light reflectance and fluorescence spectra obtained at r=260 μm were used for the quantitative fluorescence and spectral fitting calculations (e.g., Eqs. (5) and (7) described below). The white light reflectance spectrum obtained at r=260 and 520 μm was used for the extraction of optical properties using the spectrally-constrained diffuse reflectance method (e.g., Eqs. (9)-(11) described below).

In this example, the reflectance measurements were calibrated according to phantoms of known optical properties such that the reflectance is in absolute units of $cm^{-2}$. The fluorescence measurements were calibrated according to a Intralipid (Fresenius Kabi: Uppsala, Sweden) and added absorber liquid phantom with known $\mu_{a,x}$, $\mu_{s,x}'$ and fluorophore concentration.

In some examples, a phantom (e.g., a solid, sterilizable phantom) may be used as a pre-surgical calibration tool for an example of the disclosed probe. For example, the phantom may fluoresce in the spectral range of interest, and may also provide background optical scattering and/or absorption for reflectance calibration. The optical properties of the phantom may be measured using the probe (e.g., using simple light contact with the surface of the phantom) after absolute calibration, such as using the liquid phantom as described above. The solid phantom may provide a relative standard for fluorescence and reflectance. Since solid phantoms may be relatively stable, long-lasting and sterilizable (e.g., including quantum dots as fluorescent particles and/or titanium dioxide particles for background scattering), solid phantoms may be suitable for calibration immediately prior to surgery, which may not be possible for liquid phantoms. Determination of the quantitative relationship between probe signals measured from the solid phantom and the liquid phantom may allow the fluorescence and/or reflectance measurements of the probe to be calibrated ahead of a surgical procedure.

Example Model

An example model for modeling of fluorescence and reflectance detection as mediated by the fiberoptic geometry described above is now discussed. Although certain equations and theories are described below, the present disclosure is not intended to be limited to these specific theories or assumptions.

Much of the research concerning the extraction of fluorophore concentration involves excitation wavelength(s) where the tissue attenuation is low. The challenge here is to decouple the quantitative fluorescence from the optical properties of tissue given high optical attenuation at the excitation (relative to the emission band), since many fluorophores have their absorption peaks in the ultraviolet-to-green spectral region, where tissue absorption is high. This example model may provide a simple, closed-form, analytical model to extract the quantitative fluorescence spectrum with excitation wavelengths in regions of high absorption relative to the emission band. In order to extract the quantitative fluorescence, the tissue optical properties must be known at the excitation wavelength, which can be estimated using the spectrally-constrained diffuse reflectance technique. Fluorophore concentrations can then be extracted from the quantitative fluorescence spectrum through spectral decomposition using a priori fluorescence emission basis spectra. The basis spectra are essentially the shapes of the component fluorescence spectra. The fluorescence model may be implemented in the device and system described above. The example model may be useful for investigations into aminolevulinic acid (ALA)-induced protoporphyrin IX (PpIX) tumor contrast for guided resection surgery of brain tumors, for example; hence, PpIX is used as the target fluorophore in this example.

Figure 7:
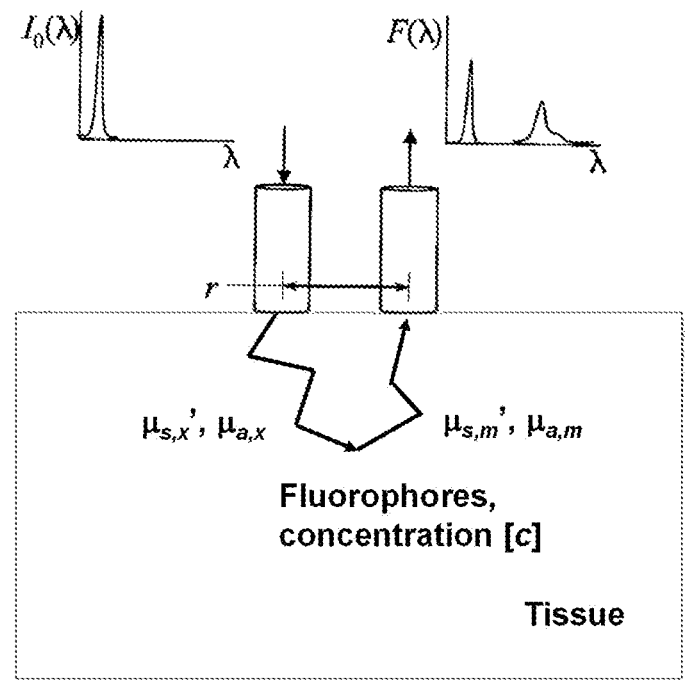
FIG. 7 shows a schematic of example fiberoptic-mediated fluorescence detection.

FIG. 7 shows a schematic of example fiberoptic-mediated fluorescence detection. Excitation light (usually a narrow wavelength band, e.g., <50 nm wide) enters the tissue through the source fiber and undergoes transport scattering and optical absorption according to the excitation optical properties, $\mu_{s,x}'$ and $\mu_{a,x}$. If and when excitation photons are absorbed by fluorophores in the tissue (in this example, it is understood or assumed to be uniformly distributed throughout the tissue at a concentration [c]) some of the photons are re-emitted as fluorescence photons according to the fluorophore's quantum yield. The emission photons are isotropically radiated and are transported through the tissue according to the emission optical properties, $\mu_{s,m}'$ and $\mu_{a,m}$. Fluorescence emission is collected by an optical fiber at a distance r away.

The following fluorescence model is based on (but not limited to) the assumption that the optical absorption at the excitation wavelength, $\lambda_x$, is high relative to that at the emission wavelength, $\lambda_m$. This is generally true in tissue if the excitation wavelength is in the UV-blue-green end of the visible spectrum (~350-575 nm) and the emission wavelength is >600 nm. As a result, the fluence rate distribution at the excitation wavelength is extremely close to the fiberoptic source; therefore, most fluorophore absorption events occur close to the source fiber. The migration paths of the fluorescence photons at $\lambda_m$ can then be approximated as the migration paths of the reflectance photons at $\lambda_m$ emitted and collected using the same fiberoptic geometry. It follows from this that the measured fluorescence, $F_{x,m}$, has a linear relationship with the diffuse reflectance at the emission wavelength, $R_m$, with both fluorescence and reflectance measured using the same geometry:

$$F_{x,m} = SR_m, \quad (1)$$

where the term, S, denotes the fraction of photons that are re-emitted as fluorescing photons from the total number of excitation photons launched into the tissue.

The term S can be modeled as the fraction of the total excitation photons that are retained within the tissue at steady-state, $S_1$, multiplied by the fraction of the total absorbed photons that are re-emitted as fluorescence photons, $S_2$. At steady-state, the number of excitation photons retained within the tissue is equal to the photons that are not diffusely reflected out of the tissue. The fraction of excitation photons that are diffusely reflected is the total diffuse reflectance, $R_{t,x}$, which depends on the internal reflection parameter, $\kappa=(1+r_{id})/(1-r_{id})$ (due to index mismatch between tissue and the external medium), and the reduced albedo at $\lambda_x$, $a_x'=\mu_{s,x}'/(\mu_{a,x}+\mu_{s,x}')$, which is given by diffusion theory (Flock et al., 1989):

$$R_{t,x} = \frac{a_x'}{1 + 2\kappa(1-a_x') + \left(1+\frac{2\kappa}{3}\right)\sqrt{3(1-a_x')}}. \quad (2)$$

An empirical formulation of $r_{id}$ for index-mismatched boundaries has widely been used, where $r_{id}=-1.44n_{rel}^{-2}+0.71n_{rel}^{-1}+0.67+0.0636n_{rel}$, and $n_{rel}=n_{tissue}/n_{external}$ (Groenhuis et al. 1983). For matching internal and external refractive indices, $\kappa=1$. In this example, matched indices were assumed. The blackened (with ink) epoxy surrounding the fibers in the probe acts as the external medium, and the ink-epoxy is assumed to be approximately index-matched to tissue. $S_1$ is the fraction of photons that are not diffusely reflected out of the tissue, so $S_1=(1-R_{t,x})$.

The quantitative fluorescence, $f_{x,m}$, is defined here as the product of the wavelength-dependent fluorescence quantum yield, $Q_{x,m}$, and the fluorescence absorption coefficient at the excitation wavelength, $\mu_{af,x}$, and is therefore an intrinsic property of the tissue, rather than a function of the collection geometry. The fraction of total absorbed photons that undergo fluorescence conversion, $S_2$, is simply the quantitative fluorescence divided by the total absorption:

$$S_2 = \frac{Q_{x,m}\mu_{af,x}}{\mu_{a,x}} \quad (3)$$

The measured (uncorrected) fluorescence can now be expressed as:

$$F_{x,m} = (1-R_{t,x})\left(\frac{Q_{x,m}\mu_{af,x}}{\mu_{a,x}}\right)R_m \quad (4)$$

If the fluorophore absorption contribution is negligible compared to the tissue absorption, i.e. $\mu_{af,x}<<\mu_{a,x}$, then $\mu_{a,x}$ can be approximated to be the same as the background tissue absorption alone. A closed form equation for the quantitative fluorescence is:

$$f_{x,m} = Q_{x,m}\mu_{af,x} = \left(\frac{\mu_{a,x}}{1-R_{t,x}}\right)\left(\frac{F_{x,m}}{R_m}\right) \quad (5)$$

Clearly, if $\mu_{a,x}$ goes to zero, the corrected, quantitative fluorescence, $f_{x,m}$, should not go to zero. Recall the underlying assumption that is high—Eq. (5) would be invalid at low excitation absorption. This negates the possible scenario of $\mu_{a,x}=0$. Note that the quantitative fluorescence spectrum has absolute units of $nm^{-1}cm^{-1}$.

Modifications to this fluorescence model are possible. For example, the above model may be modified in order to accommodate proper operation for interstitial measurements in addition to tissue surface measurements. This may be accomplished, for example, by forming a model of the total diffuse reflectance using an interstitial geometry. In another example, the model may be modified to accommodate an angled or tapered tip geometry, such as where an angled tip is used in the probe to help improve the ability of the probe to push through tissue for interstitial measurements. As well, the $S_1$ factor may be computed using another means other than diffusion theory, such as the Monte Carlo technique. In addition, if the fluorescence and reflectance do not perfectly scale linearly with each other (as in Eq. (1)), a correction factor $S_3$ may be included to compensate for cases where the assumption that the fluorescence photon migration paths are similar to the reflectance photon migration paths does not hold. $S_3$ may be derived via diffusion theory, Monte Carlo or empirical techniques.

Eq. (5) yields an emission spectrum, $f(\mu_m)$, that can be used to quantify fluorophore concentration, c, given an a priori fluorescence basis spectrum, $b(\lambda)$, equivalent to one concentration unit [µg/mL]. The relation is:

$$f = bc, \quad (6)$$

where f and b are $f(\lambda)$ and $b(\lambda)$ in column vector form. Taking the pseudo-inverse gives c:

$$c = (b^T b)^{-1} b^T f \quad (7)$$

Generalizing to N fluorophores with distinct spectra, a basis matrix, $B = [b_1\ b_2\ \ldots\ b_N]$, can be built with the individual fluorophore basis spectra as its columns, with a corresponding fluorophore concentration vector, $c = [c_1\ c_2\ \ldots\ c_N]^T$. Solving for c:

$$c = (B^T B)^{-1} B^T f \quad (8)$$

Some assumptions in this example fluorescence model include:

1. Reflectance photons and fluorescence photons traverse similar path lengths given the same fiberoptic distance, given that $\mu_{a,x} \gg \mu_{a,m}$, which is generally true if the excitation wavelength is in the high absorption band of hemoglobin (UV-blue-green) and the emission wavelength is in the red-to-near infrared (NIR).

2. $\mu_{a,x} \gg \mu_{af,x}$. In many cases, the fluorophore contribution to $\mu_{a,x}$ may be small compared to the high absorption of hemoglobin in the range of about 350-600 nm, but this should be considered based on the expected maximum concentration of the fluorophore of interest.

Figure 8:
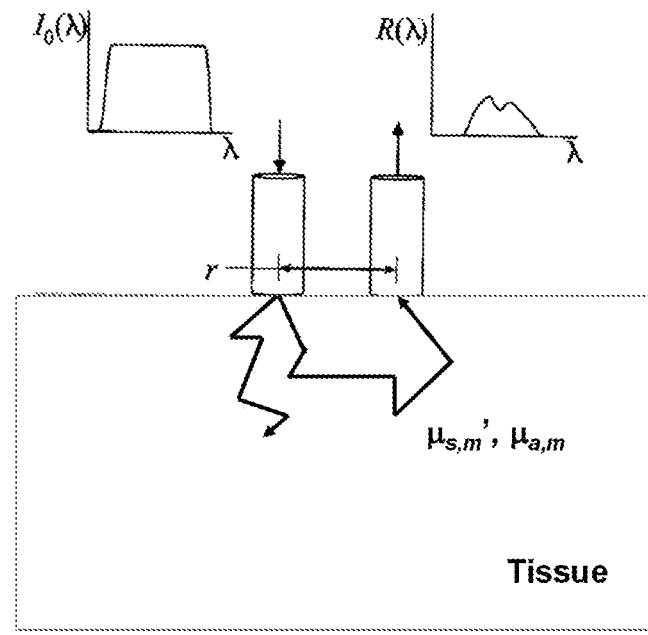
FIG. 8 shows a schematic of another example fiberoptic-mediated reflectance detection.

The fluorescence model of Eq. (5) requires the excitation tissue optical properties, $\mu_{a,x}$ and $\mu_{s,x}'$. A method that we have established to measure the optical properties employs a fiberoptic source-collector pair to measure the steady-state diffuse reflectance spectrum, as shown in FIG. 8. The following describes this technique, which may be referred to as spectrally-constrained diffuse reflectance.

FIG. 8 shows a schematic of example fiberoptic-mediated reflectance detection. A broad-band excitation is directed into the tissue via a source optical fiber. The broad-band excitation is generally a white light with potentially some content in the near infrared to infrared spectral region, for example in the order of 450-850 nm wide. The light undergoes transport scattering and absorption through the tissue that is wavelength dependent. Here, the optical properties are denoted as $\mu_{s,m}'$ and $\mu_{a,m}$, where the emission wavelength m represents any one wavelength in the excitation broad-band. The wavelength-dependent reflectance spectrum is measured by a collector optical fiber at a distance r from the source fiber. Although there may be fluorescence events here, they are considered to be negligible compared with the signal strength from the reflectance photons.

The source fiber delivers broadband white light in the spectral range of interest and the diffuse reflectance spectrum is detected by the collector fiber located at a radial distance, r, from the source, and measured using a spectrometer. Since there is only one reflectance measurement per wavelength, solving for $\mu_a(\lambda)$ and $\mu_s'(\lambda)$ relies upon spectral constraint, that is, using a priori knowledge of the shapes of the absorption and scattering coefficient spectra in the forward model. The concept here is to determine $\mu_a(\lambda)$ and $\mu_s'(\lambda)$ over a spectral range (e.g., 450-850 nm) to provide a good model fit, then extract $\mu_a(\lambda)$ and $\mu_s'(\lambda)$ by extrapolating to the excitation wavelength, which in this example $\lambda_x = 405$ nm. Using this approach to find the tissue optical properties requires caution that the absorption contributions of the fluorophores do not significantly distort the reflectance signal, and thereby the model-based curve-fitting described below.

The absorption spectrum can be modeled as a linear combination of the separate chromophore contributions. Here, it is expressed using total hemoglobin concentration [g/L] and an oxygen saturation term:

$$\mu_a(\lambda) = c_{Hb}[StO_2 \mu_a^{oxyHb}(\lambda) + (1 - StO_2)\mu_a^{deoxyHb}(\lambda)], \quad (9)$$

where $\mu_a^{oxyHb}(\lambda)$ and $\mu_a^{deoxyHb}(\lambda)$ are the wavelength-dependent absorption coefficients of oxygenated hemoglobin, and deoxygenated hemoglobin, respectively, for a concentration of 1 g/L. $c_{Hb}$ is the total hemoglobin concentration and $StO_2$ is the oxygenation fraction. Here, water is considered negligible in the range 450-850 nm.

The reduced scattering coefficient spectrum from bulk tissue has been shown to fit well to a simple wavelength-dependent power law, given by $$\mu_s'(\lambda) = A\lambda^{-b} \quad (10)$$

where A and b are constants.

The a priori knowledge of the chromophore and scatterer spectra are then combined in a forward model of the diffuse reflectance and a Levenberg-Marquardt algorithm is then applied to extract the free parameters. A simple approach to develop a forward model is to use the diffusion theory equation for spatially-resolved, steady-state diffuse reflectance, R. Here, the radial distance, r, is fixed and the optical properties $\mu_a(\lambda)$ and $\mu_s'(\lambda)$ vary according to wavelength:

$$R(\lambda) = \frac{a'}{4\pi}\left[ z_0\left(\mu_{\text{eff}} + \frac{1}{\rho_1}\right)\frac{e^{-\mu_{\text{eff}}\rho_1}}{\rho_1^2} + (z_0 + 2z_b) \left(\mu_{\text{eff}} + \frac{1}{\rho_2}\right)\frac{e^{-\mu_{\text{eff}}\rho_2}}{\rho_2^2} \right], \quad (11)$$

where $z_0 = 1/\mu_s'$, $\mu_{\text{eff}}(\lambda) = \sqrt{3\mu_a(\lambda)\mu_s'(\lambda)}$, $\mu_a(\lambda)$ and $\mu_s'(\lambda)$ are given by Eqs. (9) and (10), $\rho_1^2 = z_0^2 + r^2$ and $\rho_2^2 = (z_0 + 2z_b)^2 + r^2$. The parameters $z_0$, $r_1$, $r_2$, $z_b$ and $\mu_{\text{eff}}$ are all wavelength-dependent. The $z_b$ factor depends on $\mu_a$, $\mu_s'$ and the internal reflection parameter $\kappa$. The extrapolated boundary distance is given by $z_b = 2\kappa D$, where D is the diffusion constant given by $D = (3\mu_s')^{-1}$. This version of the diffusion constant was selected for reasons given in previous studies on the measurement of tissue optical properties. For matching internal and external refractive indices, $\kappa = 1$, which was assumed in this example, although this is not a requirement in general.

The free parameters are, therefore, the total hemoglobin concentration, oxygen saturation and scattering parameters. This is not quite as simple as applying the inverse algorithm to any r; for each r, there is a range of validity that is constrained by the peak of the reflectance versus $\mu_s'$ curve, and the diffusion model breakdown at low $\mu_s'$. By using reflectances measured at several r, the ranges of validity overlap, thus increasing the total dynamic range. In this example, r=260 and 520 µm were selected. It has been found that for these values of r, the validity range for the spectral constraint technique was $\mu_s' = 10.1$-$47.4$ cm$^{-1}$. FIG. 11 shows the lower and upper bounds of $\mu_s'$ (for $\mu_a < 10$ cm$^{-1}$) where each fiberoptic distance is valid (e.g., for r=260, 520 and 780 µm, the 780 µm distance shown to demonstrate how a longer distance does expand the overall dynamic range).

The r=260 and 520 µm source-collector distances were used because in this example the brain is the target site of interest and the brain optical properties have been measured as within this range of validity in previous laboratory experiments on murine tissues.

Variations to the described reflectance model may be possible. For example, as in the case with the fluorescence model, the above reflectance model may be modified in order to accommodate proper operation for interstitial measurements in addition to tissue surface measurements. This may be accomplished, for example, by forming a model of the diffuse reflectance using an interstitial geometry. In another example, the model may be modified to accommodate the geometry of an angled or tapered probe tip, for example where the probe has an angled tip to help the probe to push through tissue in order to take interstitial measurements. Further, as with the quantitative fluorescence model, the light-tissue interaction may be modeled with diffusion theory, Monte Carlo techniques or empirical techniques.

A technique that was found to relatively accurately determine the optical properties is to calculate $\mu_a(\lambda)$ and $\mu_s'(\lambda)$ for each fiberoptic distance (in this example, this is r=260 and 520 μm) and to determine which r distance to use for the calculation by checking if the $\mu_s'(\lambda)$ value falls within the upper and lower bounds of validity (for example, as shown in FIG. 11).

Example Studies
Phantom Studies

Phantom experiments were carried out to validate the example fluorescence model described above. Intralipid fluid (Fresenius Kabi, Uppsala, Sweden) was used to provide background scattering. Yellow food coloring (McCormick Canada, London, ON, Canada) was used to vary the absorption coefficients. Protoporphyrin IX extract (Sigma-Aldrich) was used as the target fluorophore. A set of nine phantoms were mixed, giving the optical properties shown in FIG. 12.

PpIX was mixed in six concentrations (5, 2.5, 1.25, 0.625, 0.3125, 0.15625 μg/mL) for each set of nine phantoms, for a total of 54 phantoms. Probe measurements were taken in each of the 54 phantoms, and Eq. (5) applied to the data to extract the quantitative fluorescence spectra and the PpIX concentration. As well, images of the liquid phantom surfaces in blackened cuvettes were taken using a fluorescence stereomicroscope (MZ FLIII: Leica, Wetzlar, Germany) to determine the fluorescence image intensity variation at [PpIX]=5 μg/mL.

This set of experiments was used to validate the example fluorescence model in Eq. (5) and (7), with a priori knowledge of the excitation optical properties. The measured fluorescence spectra, $F_{x,m}(\lambda_m)$ for the set of nine phantoms A-I, all with a PpIX concentration of 5 μg/mL, is shown in FIG. 13a. The raw measurements of FIG. 13a have not been corrected for optical properties variations. Applying Eq. (5) to the data produces the quantitative fluorescence spectra, f ($\lambda_m$), shown in FIG. 13b, with correction for the effects of optical properties. The relative standard deviation (normalized to the mean) at the 635 nm peak is 53.1% for the measured fluorescence and 10.1% for the quantitative fluorescence estimate.

Figures 12, 13:
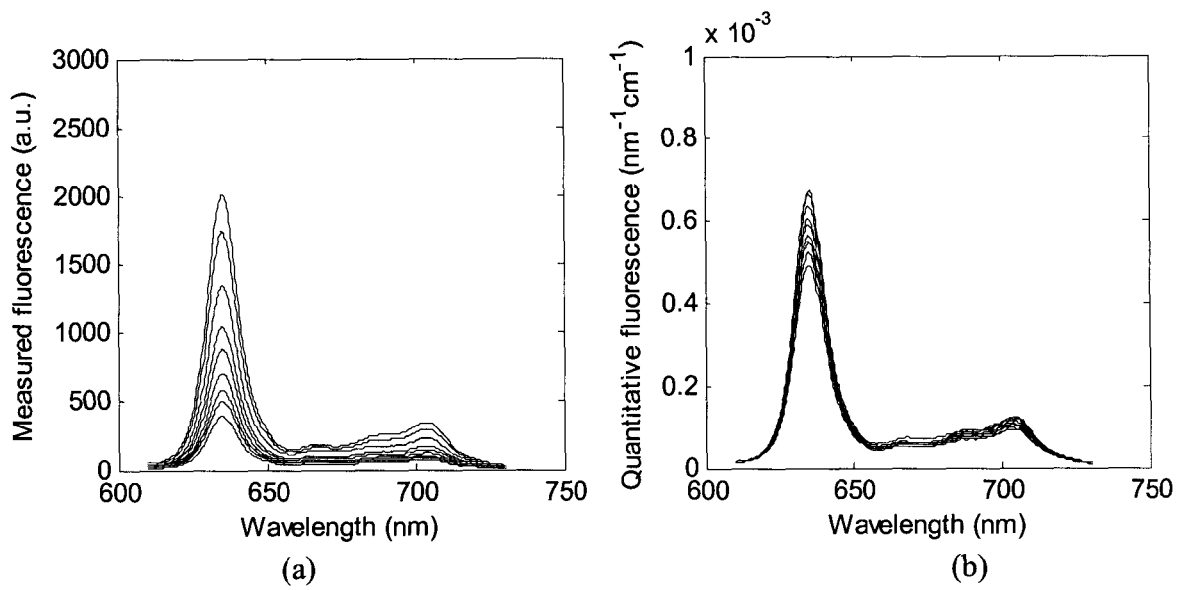
FIG. 12 is a table showing phantom optical properties for an example study of an example system and method for quantifying optical properties.
FIG. 13 shown example phantom fluorescence spectra (a) uncorrected for optical properties variation and (b) corrected for the effects of the optical properties.
Figure 14:
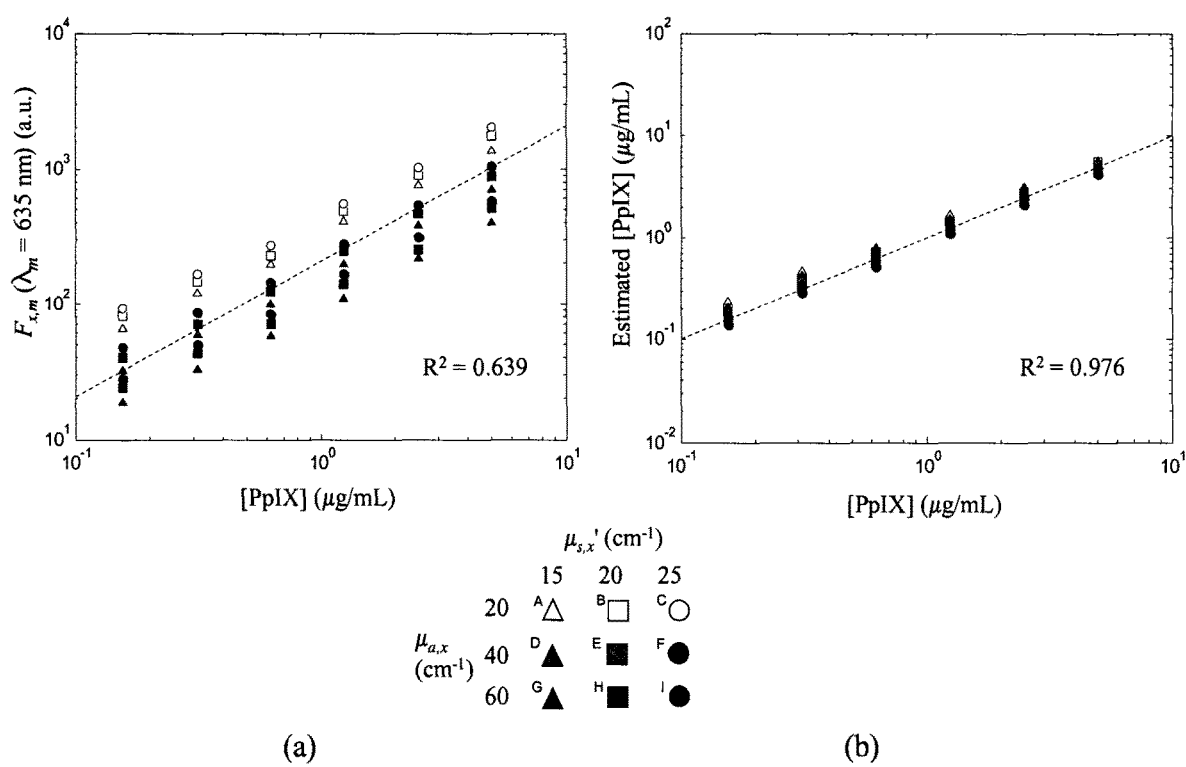
FIG. 14 shows a) measured fluorescence and b) estimated fluorophore concentration versus true PpIX concentration, from an example study.

The quantitative fluorescence model was applied to the entire data set of 54 phantoms, with the results plotted against PpIX concentration. FIG. 14a shows the measured, raw fluorescence intensities at 635 nm, compared to the estimated [PpIX] concentration shown in FIG. 14b, calculated from the raw data using Eqs. (5) and (7). The dashed line in a) represents the best straight line fit through the origin to the data; the dashed line in b) is the unity line. $R^2$ calculations were performed on the linear form of the data plot, not the log-log relation. The measured probe signal $F_{x,m}(\lambda_m=635$ nm) was curve-fitted to a linear model with [PpIX] on the x-axis in FIG. 14a. The [PpIX] probe estimate was compared to the known [PpIX] in FIG. 14b. The root-mean-square (RMS) variation from the mean, and maximum deviation from the mean were calculated from the data at 5 μg/mL (FIG. 13). The RMS error and maximum error were normalized by the mean. Using the quantitative fluorescence model and spectral fitting, the estimated [PpIX] concentration has an RMS deviation of 10.1% and a maximum deviation of 14.2%, representing a significant decrease in error from the uncorrected fluorescence measurement (RMS deviation 52.3% and maximum deviation 94.9%).

Figure 15:
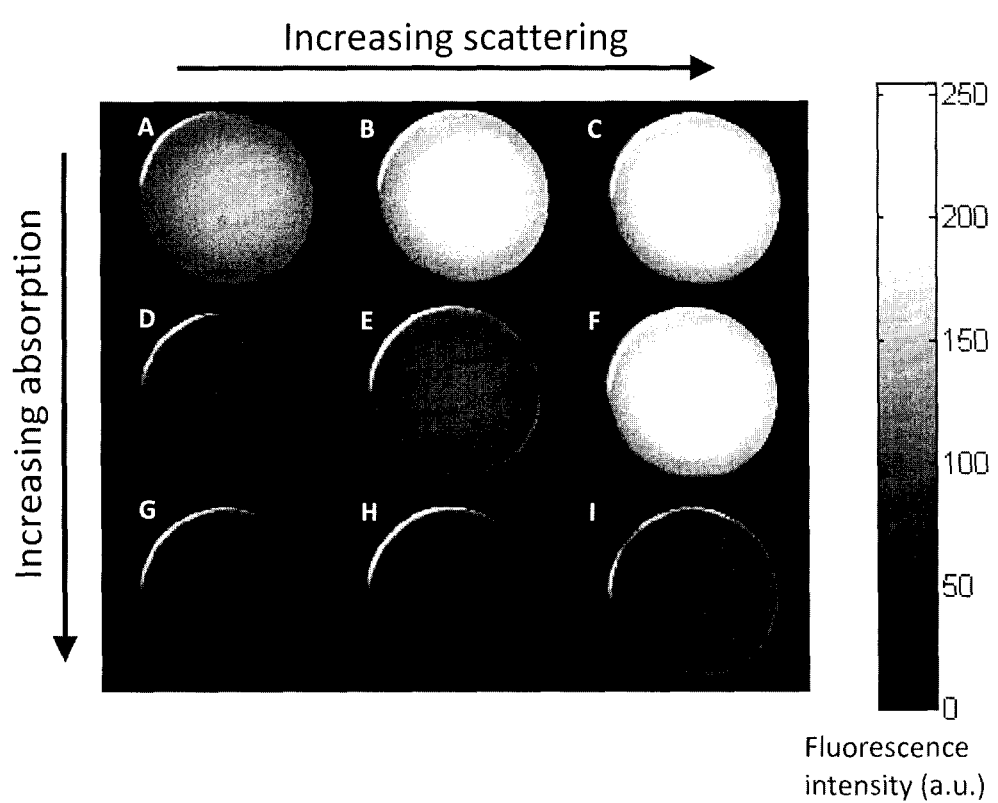
FIG. 15 shows images of example PpIX phantoms A-I.

Fluorescence microscope images of the phantoms were taken in order to get a visual conception of the fluorescence intensity variation due to changes in optical properties. Phantom surface images are shown in FIG. 15 for [PpIX]=5 μg/mL, the intensity differences between phantoms may be easily distinguishable by eye. The most significant intensity difference in this set of images is between phantom C (highest $\mu_{s,x}'$, lowest $\mu_{a,x}$) and G (lowest $\mu_{s,x}'$, highest $\mu_{a,x}$), where the fluorescence intensity of C is 4.0 times that of G.

Mouse Model

In another example study, a mouse tumor model was used to validate the example probe's accuracy in measuring photosensitizer concentrations in various tissue types, with PpIX as the target marker. The probe estimate of [PpIX] was compared with measurements of diluted, solubilized tissue in a cuvette-based fluorometer, based on a published protocol (Lilge et al., 1997)

Tumor Induction: Five male mice (20 grams) were anesthetized with 2% isoflurane and placed on a warming blanket. The skin at the injection site was swabbed with 70% ethanol, and $10^6$ B16 melanoma cells in 20 μL of phosphate buffered saline were injected subcutaneously into the left flank. Tumors were allowed to grow 4-6 mm over 7 days.

PpIX Measurement in Various Organ Tissues: After tumors had grown to size, each mouse was injected via tail vein with 100 mg/kg ALA at 0.5, 1, 2, 3 and 4 hours prior to sacrifice. The different time points were selected to ensure a large range of [PpIX] in each tissue. The mice were sacrificed by cervical dislocation while under isoflurane anesthesia. The tissue types of interest (brain, heart, kidney, liver, muscle, skin and tumor) were rapidly excised under subdued lighting conditions and three probe measurements taken per tissue sample. The samples were weighed, placed into cryotubes and then snap frozen in liquid nitrogen. The samples were stored at −70° C. in a light-tight container until ready for the tissue solubilisation procedure.

Tissue Solubilisation Protocol: A tissue solubilisation protocol was used to measure the absolute fluorophore concentration (Lilge et al, 1997). Each tissue sample was combined with 2 mL of Solvable and placed in an undulating water bath at 50° C. for 1 hour. The tissue/Solvable solution was homogenized with a Tissue Tearor tool (Biospec Products, Bartlesville, Okla., USA) in the original vial. 200 μL of the tissue homogenate was combined with 3 mL of distilled water and 1 mL of Solvable. This solution was incubated in the water bath at 50° C. for 1 h. The optical density was measured and diluted down to <0.1 if necessary. The resulting solution was transferred to a quartz cuvette. The cuvette was analysed via fluorometer (Fluorolog: Jobin Yvon, Edison, N.J., USA), using an excitation wavelength of 401 nm. A look-up curve was constructed by measuring known concentrations of PpIX in 75/25 distilled water/Solvable solution, with the detector nonlinearity taken into account for the [PpIX] calculations.

Figure 16A:
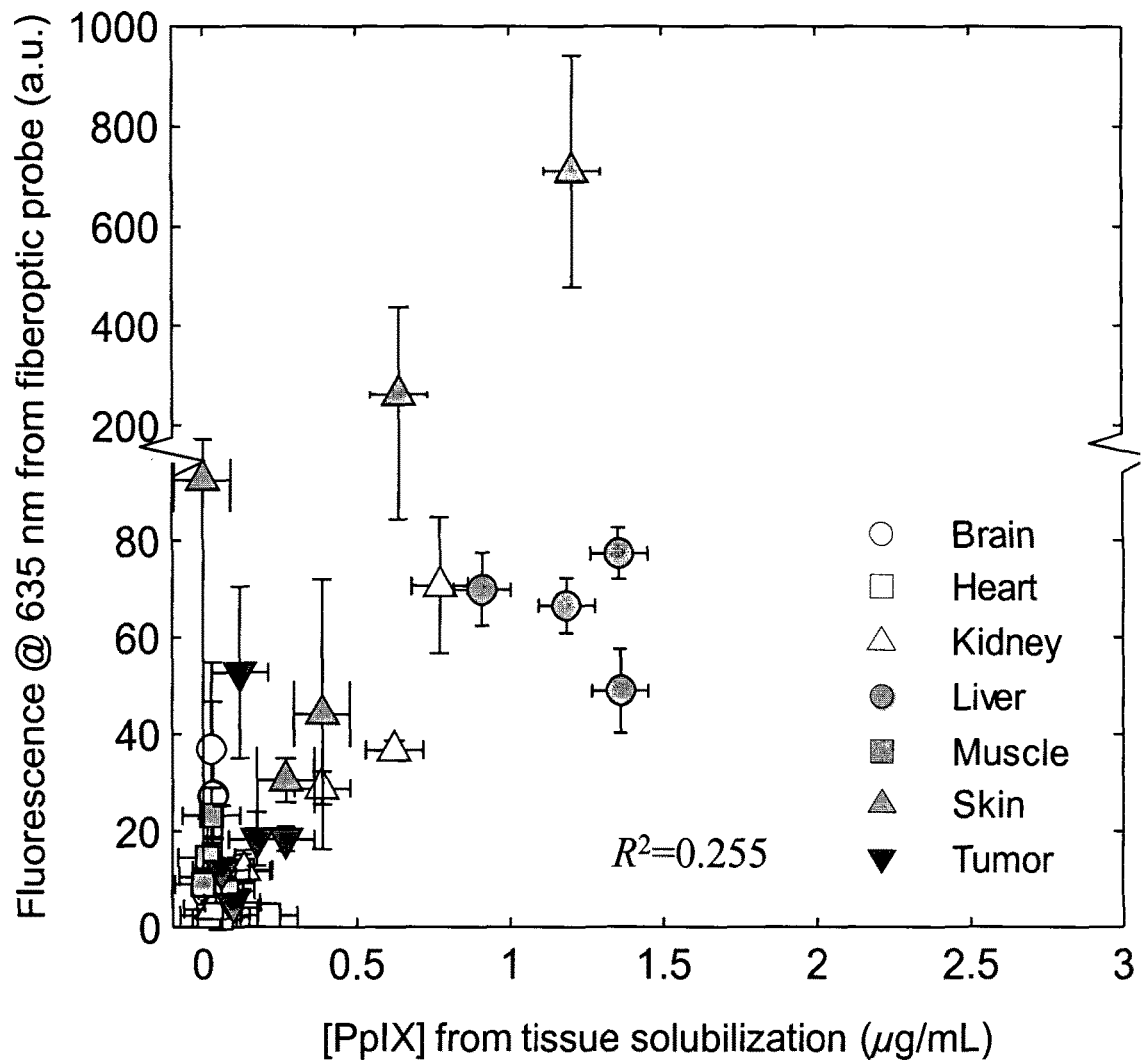
FIGS. 16A and 16B displays fluorescence measurements from an example ex vivo mouse experiment.
Figure 16B:
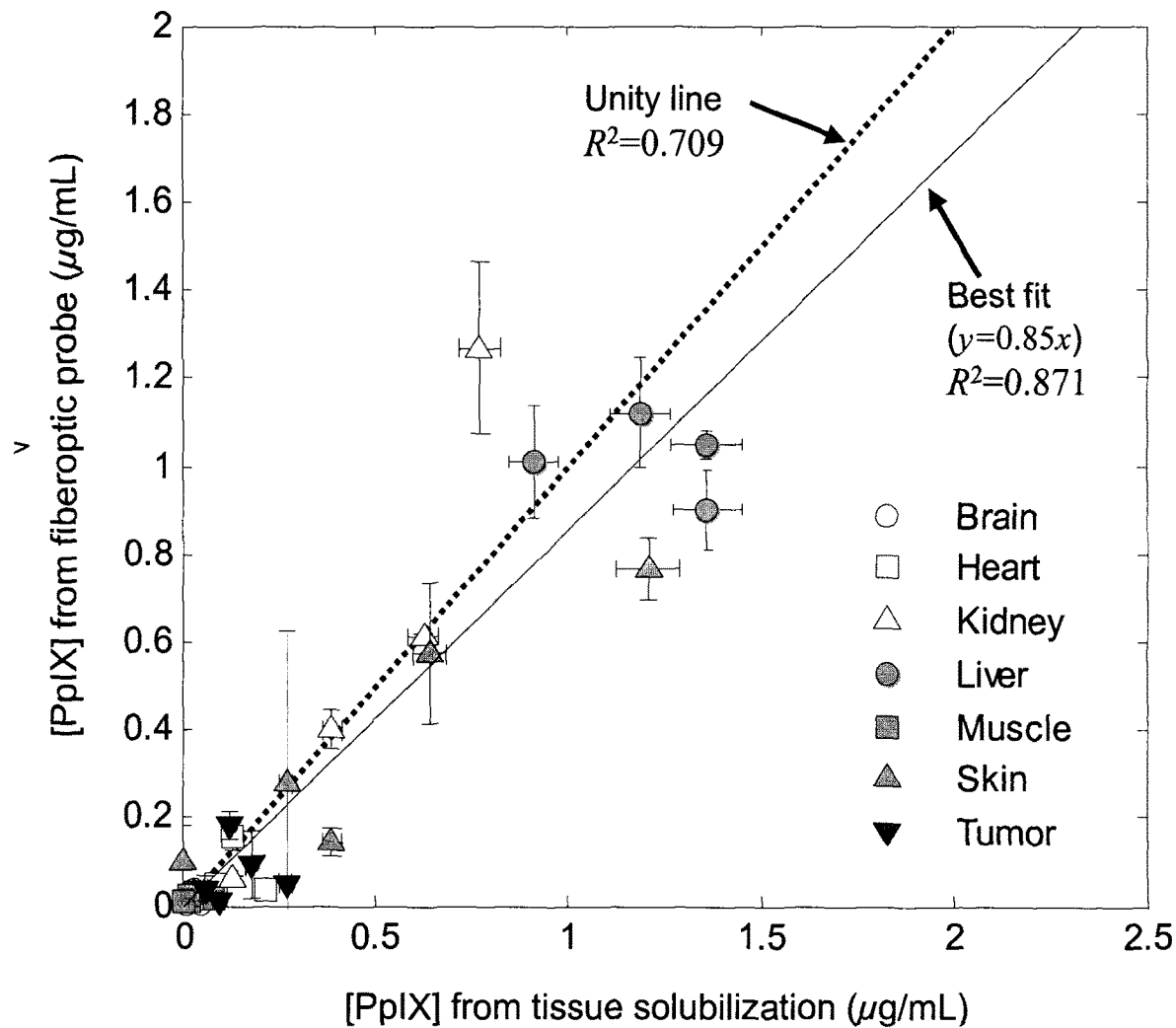

FIG. 16a shows the measured (i.e., uncorrected) fluorescence signal exemplified by the PpIX peak at 635 nm plotted against the [PpIX] measurement from the tissue solubilisation technique for 34 tissue samples. The y-axis has been re-scaled mid-figure to better visualize the higher-value data. The data show significant scatter, with little correlation between the x- and y-axes. Applying the example correction algorithms described above to the data, the resulting [PpIX] estimate from the fiberoptic probe has improved correlation with the [PpIX] measurement from the tissue solubilisation technique (FIG. 16b), demonstrating that the example fiberoptic probe an associated model and method described above may be useful for quantifying fluorophore content in tissue. In FIG. 16a and FIG. 16b, y-axis error bars are standard deviation bars from three measurements on each tissue sample; x-axis error bars were calculated from the root-mean-square (RMS) error percentage from accuracy statistics of the solubilisation protocol (Lilge et al., 1997), multiplied by 0.5 of the maximum [PpIX] measured via tissue solubilisation in this mouse tissue experiment.

Example Patient Study

Another example study is now described. In this example study, 14 patients with a variety of intracranial pathologies (including low- and high-grade gliomas, meningioma, and intracranial lung metastases, as indicated in FIG. 17) were administered 20-mg/kg of ALA 3 hours prior to induction of anesthesia. The neurosurgeon performed a conventional standard craniotomy procedure with image-guidance using a surgical microscope modified for PpIX fluorescence. At the surgical bed, the surgeon acquired multiple sets of measurements using an example probe, with corresponding tissue specimens collected and processed for histopathological analysis. In each case, the surgeon acquired probe measurements of normal brain tissue as controls. In addition, the surgeon scored the visible fluorescence as viewed through the fluorescence-capable surgical microscope (scores from 0-4). All specimens were assessed as either normal or abnormal, such that presence of tumor cells was assessed as abnormal. The total numbers of control and biopsy sites are listed in FIG. 17.

Statistical significance tests, linear discriminant analysis and receiver-operator characteristic analysis were performed on this in vivo data set acquired by the example quantitative fluorescence probe.

Statistical Significance Tests: Since the data in this example were expected to be non-parametric, a Wilcoxon rank-sum test was selected in order to determine how statistically-significant were the several optical parameters derived from the in vivo probe data at distinguishing between normal and tumor tissues. PpIX concentration was one of the parameters to be tested. In addition, the following optical parameters were tested for statistical significance in differentiating normal from tumor tissue: the autofluorescence (AF) at 600, 635, 650 and 700 nm, diffuse reflectance (for both r=260 and 520 µm fiber distance) at 575 and 600 nm, oxygen saturation ($StO_2$), total hemoglobin concentration, $f_{Hb}$, and $\mu_a$ and $\mu_s'$ at 575 and 600 nm.

Linear Discriminant Analysis: Statistically-significant optical parameters that disprove the null hypothesis according to Wilcoxon rank-sum tests were evaluated as to their physiological and photochemical relevance to brain cancer. The selected parameters were used in a linear discriminant analysis (i.e. Fisher's linear discriminant) in order to find the vector in this feature space such that the normal and tumor classes were separated to a maximal extent (at least, in a linear fashion).

Receiver-Operator Characteristic Analysis: The receiver-operator characteristic (ROC) curves were generated using the PpIX concentrations as the parameter comparing normal tissue to these tumor populations: all tumors, all gliomas, low-grade gliomas (LGGs), high-grade gliomas (HGGs), meningiomas and metastases. Optimal sensitivity and specificity values were extracted to determine performance of PpIX concentrations as a tumor-specific marker. The performance of PpIX concentrations as a tumor-specific marker was compared with a metric for the uncorrected, raw fluorescence spectrum (i.e., not corrected for optical properties), and the neurosurgeon's scoring of the visible fluorescence through the surgical microscope (scores are from 0 to 4). The uncorrected fluorescence metric was the magnitude of the PpIX fluorescence peak from the raw fluorescence spectrum, i.e. $F_{x,m}$ at 635 nm (see Eqs. 1 and 4). In this example, the three qF probe measurements at each site were used separately to calculate the ROC curve (rather than averaging the triplicate measurements at each site).

As well, ROC analysis was performed for the above pathologies using linear discriminant analysis. In other words, multiple variables that can be quantified from the probe data (e.g., PpIX concentration, oxygen saturation, hemoglobin concentration, etc.) were used to attempt to separate the normal and tumor classes to the maximum extent. Since the "training" data set used to train the LDA should not be the same as the "validation" data set used to evaluate the LDA using ROC analysis, a cross-validation algorithm was set up to assess the performance statistics. The cross-validation scheme that was used was repeated random sub-sampling validation. Essentially, half of the data set is randomly sampled and assigned as the training data set to train the LDA. The remaining half is used for validation using ROC analysis. The process was repeated several times and the performance statistics were averaged. In this example, the random sampling process was run 50 times.

Results

Figure 18:
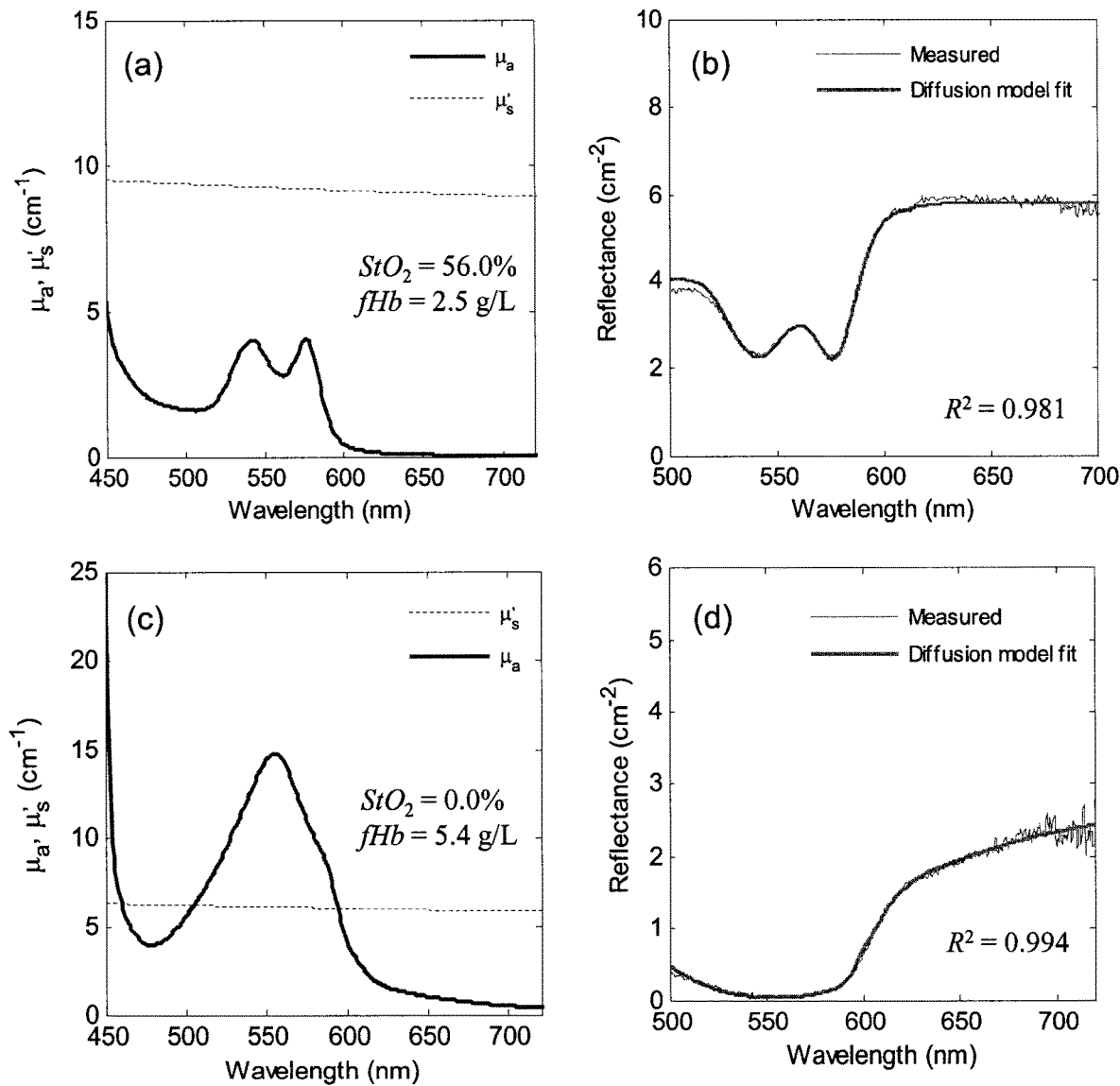
FIG. 18 shows plots of example optical properties spectra and reflectance data from an example study of an example system and method for quantifying optical properties.
Figure 19:
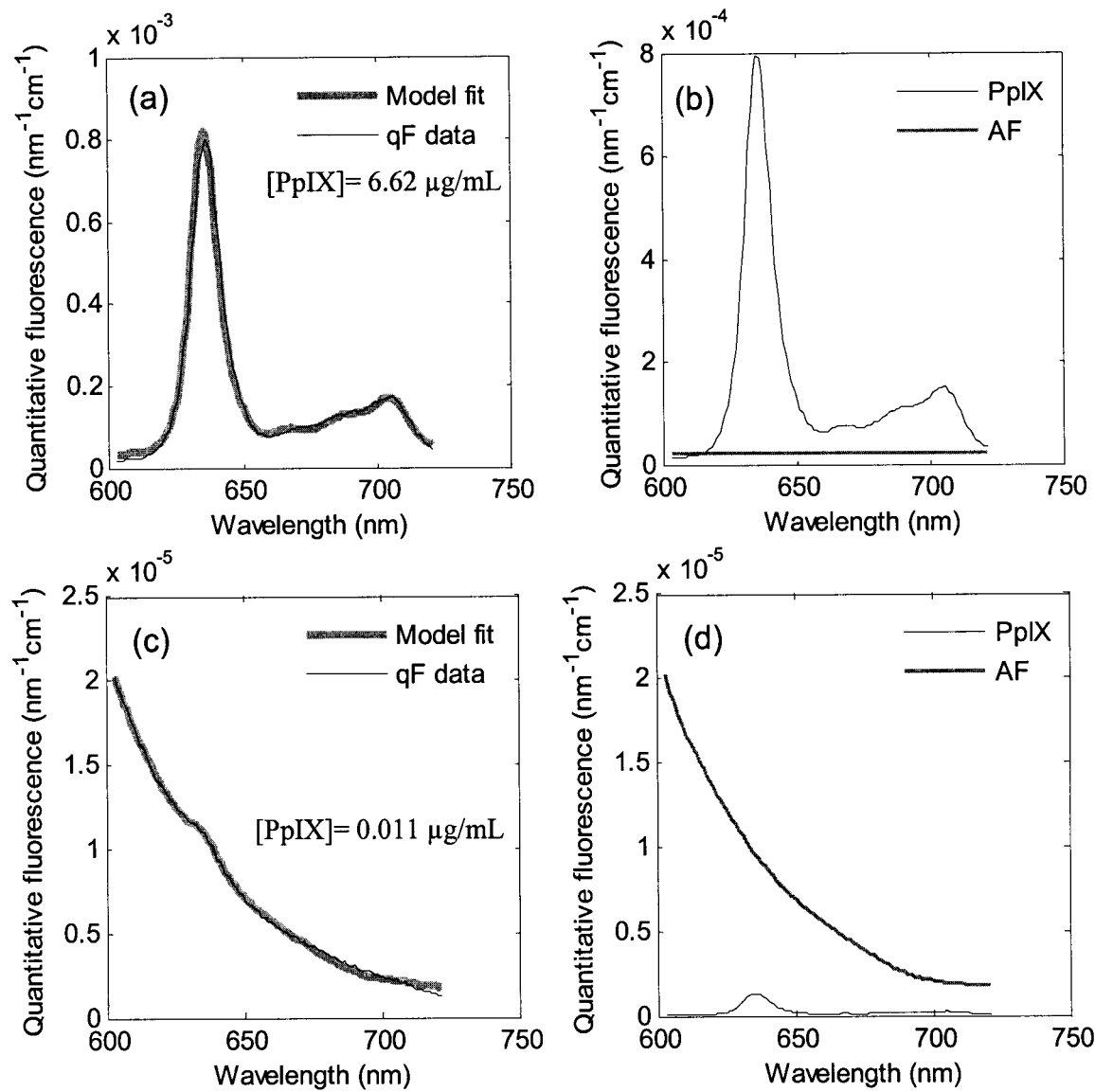
FIG. 19 shows plots of example fluorescence data from a patient with a meningioma, measured using an example device for quantifying fluorescence and optical properties.

In Vivo Probe Measurements: The data fits to the reflectance and fluorescence measurements from the handheld probe during resection surgery were generally good across all tissues. FIG. 18 displays data from an example patient with a high grade glioma (HGG) and an example meningioma patient. Panels (a) and (b) display measurement data in normal tissue (in this case, normal brain parenchyma), while panels (c) and (d) show measurement data from tumor tissue (in this case, a high-grade glioma). Panels (a) and (c) show in vivo tissue optical properties spectra, while panels (b) and (d) show reflectance data with model fit. The reflectance model fits very closely to the reflectance measurements. FIG. 19 shows quantitative in vivo fluorescence data from an example meningioma patient, as measured using an example handheld fluorescence probe. Panels (a) and (b) show data from the meningioma, while panels (c) and (d) show data from normal dura. Panels (a) and (c) show examples of the quantitative fluorescence measurement and model fit, while panels (b) and (d) show examples of the spectrally unmixed signals. The tumor data show a strong PpIX signal; however, the normal tissue data show AF in the same range as the PpIX signal. These demonstrate the usefulness of accurate AF modeling: in this neurosurgical trial, the AF was modeled as a linear combination of the spectral shapes of flavin adenine dinucleotide, nicotinamide adenine dinucleotide and lipofuscin.

Figure 20:
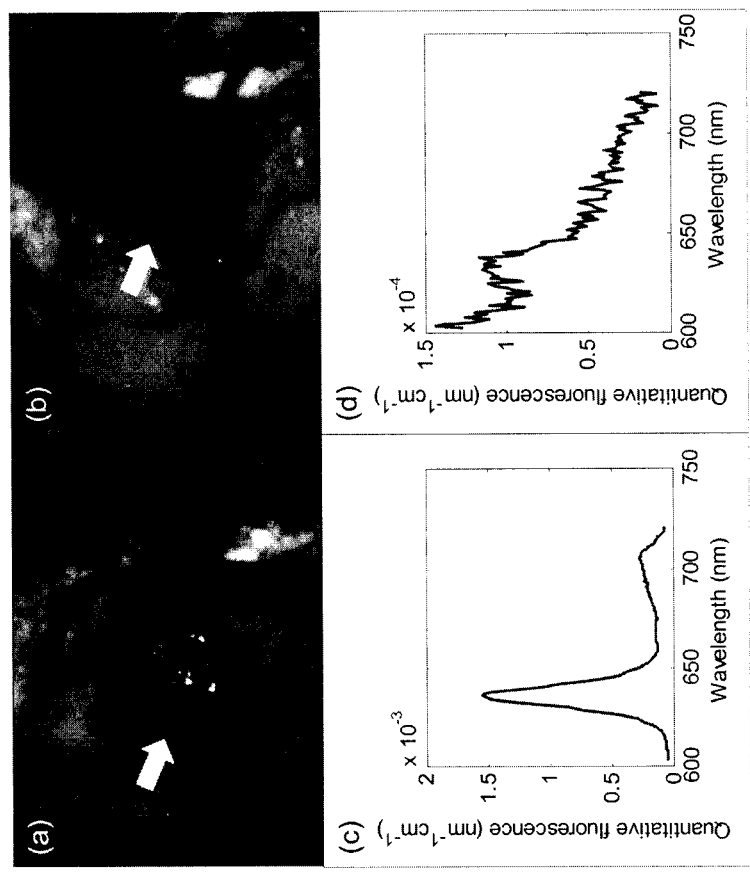
FIG. 20 shows example fluorescence images and corresponding example fluorescence spectra from a patient with a glioma, measured using an example device for quantifying fluorescence and optical properties.

FIG. 20 exemplifies the additional sensitivity to fluorescence that may be afforded by the disclosed probe as compared to the fluorescence microscope during resection surgery. In FIG. 20, images and measurements were obtained from an example low-grade glioma patient during tumor resection surgery. Panels (a) and (b) display fluorescence images from two sites in the same patient that were both histologically confirmed as tumor. Panels (c) and (d) quantitative fluorescence spectra, obtained using an example fluorescence probe, corresponding to the sites of panels (a)

and (b), respectively. The probe measurement sites are indicated by white arrows, and the probe shaft is visible at the point of contact. The first site (panels (a) and (c)) shows visible fluorescence (in this case obtained using an operating microscope), with the surgeon scoring that site as a '2'. This was confirmed by the probe measurement with [PpIX]=12.9 µg/mL. However, the second site (panels (b) and (d)), measured after the visible tumor from the first site was removed, has no visible fluorescence (surgeon's score of '0') yet there is a measureable [PpIX] of 0.36 µg/mL Both sites were histologically confirmed as tumor tissue.

FIG. 21 is a table displaying example PpIX concentrations measured in vivo by an example probe in normal and tumor tissues for the various pathologies. The table of FIG. 21 shows example comparisons of in vivo PpIX concentration levels found in normal and tumor tissues for each of the pathologies in the example study. The tumor-to-normal (T/N) ratios for all pathologies, in this example, are of the same order of magnitude and average out to T/N=200. Standard deviations are indicated by the symbol "±".

In this example, fifteen optical parameters were tested as to their statistical significance in differentiating between normal and tumor tissue in vivo. The table of FIG. 22 shows the list of example diagnostic variables that were tested for significance in differentiating between normal and tumor tissues. In this table, the value h denotes if the null hypothesis has been disproved, with '1' indicating the null hypothesis is not true and '0' indicating it is true. The range of significance levels used to reject the null hypothesis was $p<0.05$. This analysis was performed for the glioma data set and the all-tumors data set. Partly based on this, [PpIX], AF at 600 nm, the reflectance at both fiber separations at 600 nm, $StO_2$ and $f_{Hb}$ were used for the multi-variable linear discriminant analysis.

Figure 23:
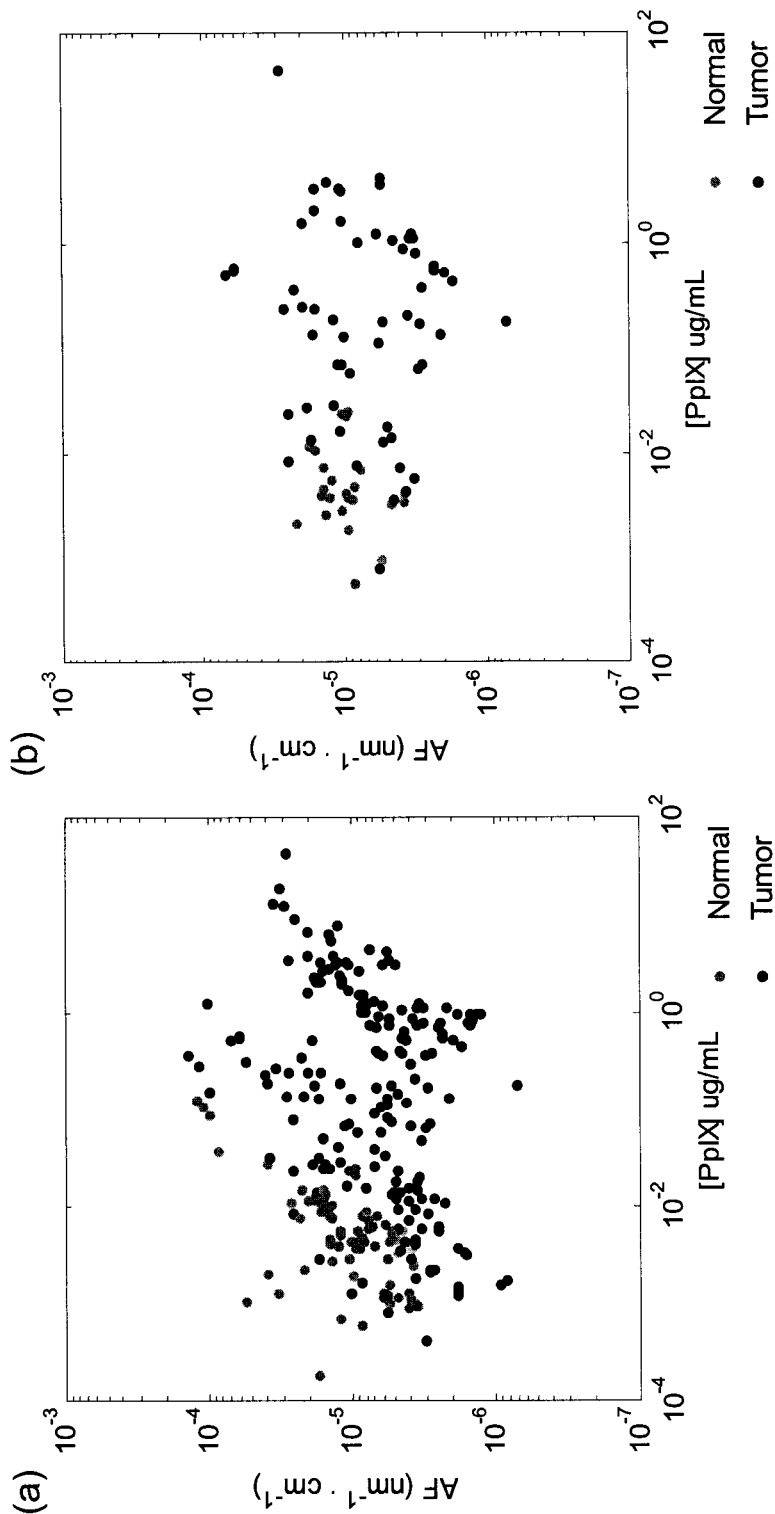
FIG. 23 shows plots of example in vivo quantitative fluorescence from an example study of an example system and method for quantifying optical properties.

There may also be physiological and photochemical reasons for these selections for multi-variable linear discriminant analysis. [PpIX] may be the chief tumor biomarker. Autofluorescence (AF) may be tumor-specific, and the autofluorescence at 600 nm (in this example, the shortest wavelength in the fluorescence data collection range) may have the strongest AF signal, since AF may peak in the green region of the spectrum, which is near 600 nm. FIG. 23 shows examples of cluster plots (for the example all-tumors data set and the example HGG data set) with AF on the y-axis and [PpIX] on the x-axis, illustrating (at least qualitatively, visually) that autofluorescence may be useful in separating the normal and tumor data clusters. In FIG. 23, (a) is a plot showing example data for all tumors studied and (b) is a plot showing example data for high-grade gliomas. Reflectance values at 600 nm may be dominated by scattering, which in turn may be affected by cell organelle size and morphology. Reflectance measurements at the two fiber separations may contain encoded information on not only the reduced scattering coefficient, but also the scattering phase function. Finally, $f_{Hb}$ and $StO_2$ may be diagnostically useful in distinguishing between glioma and normal tissues.

ROC Analysis of the In Vivo Probe Data

Figure 24:
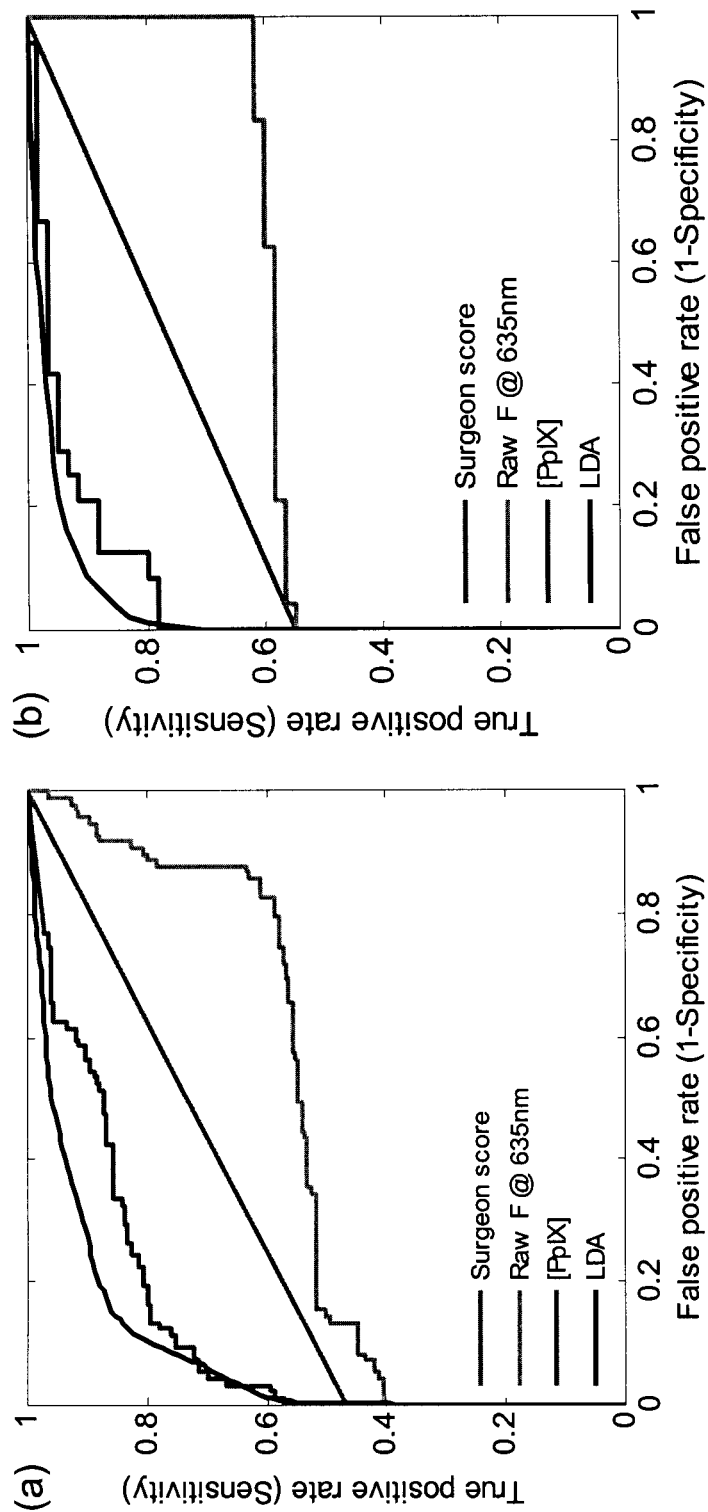
FIG. 24 shows plots of example diagnostic variables tested in an example study of an example system and method for quantifying optical properties.

FIG. 24 displays the example ROC curves for (a) the in vivo all-tumors data set and (b) the in vivo HGG data set. In FIG. 24, the example diagnostic variables considered were: the surgeon's visible fluorescence score as determined through the surgical microscope; the PpIX peak (e.g., 635 nm) fluorescence magnitude from the raw, uncorrected fluorescence spectrum; PpIX concentration; and a metric derived from linear discriminant analysis. In this example, the raw uncorrected fluorescence measurement at the 635 nm PpIX peak performed the worst of the variables studied.

The surgeon's subjective fluorescence scoring was better than the raw fluorescence metric. Note that the surgeon in this example study was relatively experienced with ALA-PpIX FGR, so the good performance of the subjective fluorescence scoring result may be unrepresentative. However, the quantitative [PpIX] metric performed better than the surgeon's scoring, with the LDA model improving the tumor detection accuracy.

FIGS. 25-29 displays example ROC in vivo data, including the ROC area under the curve (a.u.c.) data, sensitivity and specificity values for: the all-tumors (FIG. 25), HGG (FIG. 26), LGG (FIG. 27), intracranial lung metastasis tumors (FIG. 28) and meningioma (FIG. 29) data sets. In this example study, for all tissue types with the exception of metastatic tumors, the general trend holds that the order of increasing performance is: raw fluorescence at 635 nm, surgeon's score, [PpIX] and then LDA. For the lung metastatic tumor data, the ROC area-under-curve is slightly higher for [PpIX] than the LDA classifier, though both these have better performance than the surgeon's score and raw fluorescence metric.

Conclusion: In this example study an intraoperative fiber-optics probe was used to estimate PpIX concentrations in vivo during clinical intra-cranial resection procedures. Spectrally-dependent endogenous optical properties (e.g., absorption, scattering) were computed for each light collection point and used as prior information in an algorithm designed to estimate PpIX concentrations from measured fluorescence spectra.

There may be several clinical rationales for using an example of the described probe. For example, it may be used to overcome limitations of conventional fluorescence imaging techniques and instruments used (such as the lack of quantification of the fluorescence signal in a typical imaging system), for example, for surgical guidance. Thus, an example of the probe may be used to detect lower concentrations of fluorophore in tissue and provide better discrimination from the autofluorescence tissue background. An example of the probe may also provide quantitative and absolute measurements of the fluorophore concentration in the tissue. An example of the probe may also provide relatively highly localised measurements, which may be at the tissue surface or at depth. For example, depth measurements may be acquired by positioning the probe tip interstitially through the tissue, to allow interstitial measurements to be taken.

The example study described above shows evidence that probe measurements may confer greater sensitivity than the surgical microscope in detecting a significant amount of PpIX fluorescence in abnormal tissue compared to normal. In instances of no visible fluorescence as determined through the surgical microscope, probe estimates of PpIX concentrations in this study showed approximately at least five times more PpIX in abnormal tissue compared to normal tissue. It may also be useful to corroborate the diagnostic capabilities of using probe estimates of PpIX concentration as an intraoperative diagnostic tool for delineating tumor margins in ALA-PpIX FGR. This example study illustrates that quantitative measurements using the example probe may be sensitive enough to detect a significant difference between abnormal tissue (e.g., tissue with the presence of tumor cells and/or reactive changes) and normal tissue. It may be useful to note that these reactive changes may be present in the peritumoral regions and as such may provide preliminary data regarding the probe's ability to detect PpIX differences at the farthest extent of tumor margins. To summarize, the results of this example study may provide data to support using spectroscopically estimated PpIX concentrations for tumor margin delineation and in vivo diagnosis.

The diagnostic accuracy of the example probe may be further improved by considering diagnostic variables other than PpIX concentration. For example, other metrics such as reflectance, oxygen saturation, hemoglobin concentration and/or autofluorescence may be included in the diagnostic determination. FIGS. 24-29 show examples of how a diagnostic determination taking multiple diagnostic variables into account may be useful (in these example figures, linear discriminant analysis was found to generally have a relatively good diagnostic result).

Applications

The example device and system described, and associated model and method may provide useful diagnostic techniques for the operating room. For example, the fiberoptic probe may be useful as an intraoperative diagnostic tool for delineating brain tumor margins. For example, FIG. 20, panels (a) and (b) illustrate the use of the probe in a tumor site. The probe measurement sites are indicated by white arrows, and the probe shaft is visible at the point of contact.

There may be a number of biomedical applications for in situ quantitative fluorescence spectroscopy using the described device, system and method. Although the above discussion focused primarily on the use of the example fiberoptic probe to delineate glioma tumor margins during resection surgery, the probe can be used for general optical diagnosis or monitoring of tissue disease states or normal physiology. Endogenous and exogenous fluorescence contrast has been explored to detect and diagnose diseased tissue. Since tissue optical properties and measurement geometry may significantly affect the fluorescence signal, it is useful for these distorting effects be removed. The disclosed device, system and method may therefore be useful for improving current efforts to correctly diagnose or monitor tissue using fluorescence.

Another potential application is the evaluation of drug biodistribution and time kinetics in patients and pre-clinical animal models. It is often useful to know how a drug is distributed in various organs and pathological tissues for diagnostic, therapeutic or response monitoring clinical applications. Many diagnostic and therapeutic photosensitizing drugs are fluorescent, such as protoporphyrin IX (PpIX), Photofrin and benzoporphyrin derivative. Alternatively, the drug may happen to be fluorescent despite the clinical application of the drug being unrelated to fluorescence: for example, the chemotherapy drugs taxol, cyclophosphamide and doxorubicin are fluorescent. Alternatively, a drug may be made fluorescent by tagging it with a fluorescent reporter, such as binding fluorescent molecules (or molecular beacons, or nanoparticles) to chemotherapy drugs, heart medication, or other medications. It is a common goal in pre-clinical studies to measure drug content in various organs to determine the safety and efficacy of the drug. The example device and system may be useful to determine the time kinetics and biodistribution of such fluorescing drugs, such as a recent pre-clinical study done in our labs with a porphyrin dimer-based drug for two-photon absorption photodynamic therapy of melanoma tumors.

The fiberoptic probe can also be used to monitor photodynamic therapy (PDT). There are several physiological parameters that may be used to dynamically monitor PDT, such as tissue oxygenation, fluorescent drug concentration, etc. Another form of implicit PDT monitoring may be based on monitoring the generation of photoproducts of the therapy drug. PpIX has known photoproducts with spectral peaks distinct from the original fluorophore. PpIX photoproduct generation has been shown due to unintentional photodynamic therapy of brain tumors by the illumination from the neurosurgical microscope. This phenomenon may also be a useful metric for monitoring of PDT (i.e. done intentionally). Implicit PDT monitoring of oxygen and drug depletion may aid in reducing patient-to-patient variability.

In some examples, the present disclosure may be useful for radiation therapy, for example to detect target tissue for treatment and/or to assist in identifying tumor tissue for designing a radiation treatment plan. The present disclosure may also be useful for delineating margins in various tumor sites including, for example, the head and neck, the prostate, the breast, skin, and other sites.

This technique may be expanded to non-biological or non-living tissue applications, for example where fluorescence quantification may be used to test optically-turbid, fluorescent materials. Examples of such materials include but are not limited to: pulp and paper, food and beverage, paint making, plastics, lumber, food safety (e.g., detection of food-borne bacteria or pathogens that may be fluorescent or made to be fluorescent), and pharmaceuticals (e.g. pills). Fluorescence quantification may be used for quality control of materials or for human safety purposes.

Figure 9:
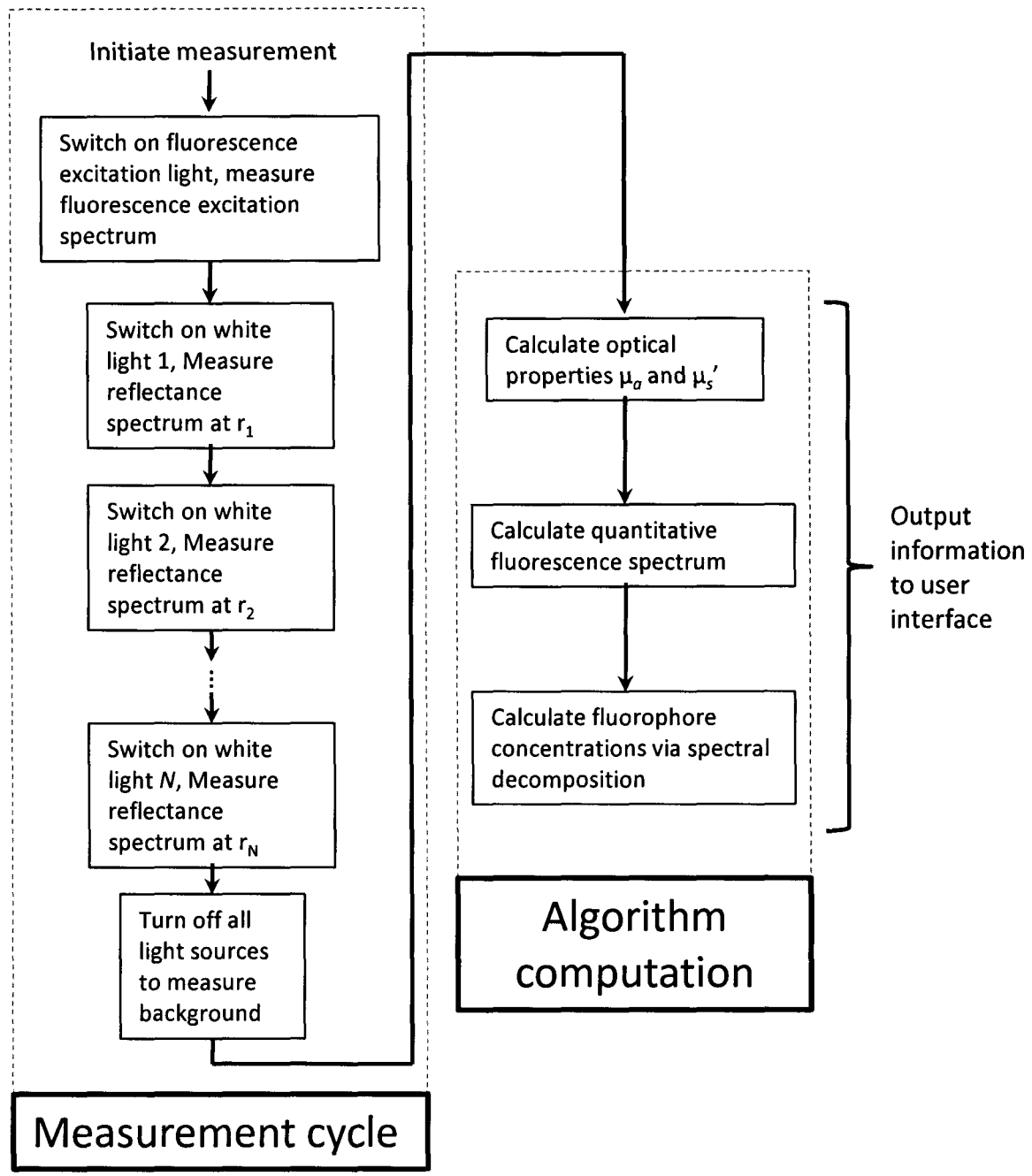
FIG. 9 is a diagram illustrating an example method for quantifying fluorescence and optical properties.

There may be additional functionality applied to the fiberoptic probe. A switch on the probe or a foot pedal may be added to trigger data acquisitions. As well, the measurement cycle and algorithm computation schematically represented in FIG. 9 may be run continuously to provide real-time information to the operator. The example shown in FIG. 9 includes measurement of: the fluorescence spectrum (at one fiberoptic distance), the reflectance spectr(a)um (at one or multiple fiberoptic distances) and the background ambient light. The diagram also outlines the example algorithm to compute the optical properties, quantitative fluorescence and fluorophore concentrations, to be elucidated in the detailed description section.

Optical tracking or electromagnetically tracking sensors may be placed on the probe to track its position and orientation with reference to other imaging modalities and surgical tools. One example with regard to surgical tumor resection is to use position tracking sensors to track the probe within a surgical cavity (e.g., a brain cavity) with reference to pre-operative MRI or CT, to correlate fluorescence point measurements with tomographic information.

Other techniques may be used to estimate the optical properties. For example, in the UV-blue region, hemoglobin absorption may be significant, so a photothermal technique (such as pulsed-photothermal radiometry or photoacoustic spectroscopy) may be used to measure the excitation absorption and scattering. Photothermal optical properties measurements have a larger dynamic range than diffuse reflectance for measuring absorption because in the former, optical absorption adds to the measurement signal whereas in the latter, absorption subtracts from the signal, which makes the maximum measureable absorption restricted by the signal-to-background contrast.

The described device, system and methods may be used where fluorescence emission is detected from a fluorescence marker, including, for example: protoporphyrin IX (PpIX) (including ALA-induced PpIX) and indocyanine green (ICG). Other suitable fluorescence markers may include, for example: an organic fluorophore (e.g., nicotinamide adenine dinucleotide, flavin adenine dinucleotide, or collagen), a nanoparticle-based agent (e.g., a quantum dot, or a nanoparticle carrying a fluorescent agent.), fluorescein and a fluorescent molecular beacon (e.g., based on enzymatic cleavage or antisense hybridization). The fluorescence marker may be targeted to a tissue of interest using a targeting moiety, such as an antibody or a peptide. The fluorescence marker may alternatively be untargeted. In some examples, the fluorescence marker may be fluorescein (e.g., for marking disrupted blood-brain barrier of a brain tumor).

Although certain examples have been described, these are for the purpose of illustration only and are not intended to be limiting. Variations, combinations, and equivalents of the specific embodiment, method, and examples herein may be possible. Features described in separate examples may be used in combination. Specific values and sub-ranges within disclosed ranges are also disclosed. The present disclosure is not necessarily bound by any theory or assumptions described by way of example. All references mentioned are hereby incorporated by reference in their entirety.

REFERENCES

1. K.R. Diamond, M.S. Patterson, T.J. Farrell. "Quantification of fluorophore concentration in tissue-simulating media by fluorescence measurements with a single optical fiber," Appl. Opt. 42(13), 2436-2442 (2003).

2. J.C. Finlay, T.C. Zhu, A. Dimofte, D. Stripp, S.B. Malkowicz, T.M. Busch, S.M. Hahn. "Interstitial Fluorescence Spectroscopy in the Human Prostate During Motexafin Lutetium-Mediated Photodynamic Therapy," Photochem. Photobiol. 82(5), 1270-1278 (2006).

3. S.T. Flock, M.S. Patterson, B.C. Wilson, D.R. Wyman. "Monte-Carlo modeling of light-propagation in highly scattering tissues: 1. Model predictions and comparison with diffusion-theory," IEEE Trans. Biomed. Eng. 36(12), 1162-1168 (1989).

4. F.A.J. Groenhuis, H.A. Ferwerda, J.J. ten Bosch. "Scattering and absorption of turbid materials derived from reflection coefficients. 1: Theory," Appl. Opt. 22(16), 2456-2462 (1983).

5. L. Lilge, C. O'Carroll, B.C. Wilson. "A solubilization technique for photosensitizer quantification in ex vivo tissue samples," J. Photochem. Photobiol. B 39(3), 229-235 (1997).

6. M.G. Müller, I. Georgakoudi, Q. Zhang, J. Wu, M.S. Feld. "Intrinsic fluorescence spectroscopy in turbid media: disentangling effects of scattering and absorption," Appl. Opt. 40(25), 4633-4646 (2001).

7. R. Sroka, W. Beyer, L. Gossner, T. Sassy, S. Stocker, R. Baumgartner. "Pharmacokinetics of 5-aminolevulinic-acid-induced porphyrins in tumour-bearing mice," J. Photochem. Photobiol. B, Biology 34(1), 13-19. (1996).

8. W. Stummer, H. Stepp, G. Moller, A. Ehrhardt, M. Leonhard, H.J. Reulen. "Technical principles for protoporphyrin-IX-fluorescence guided microsurgical resection of malignant gliomas tissue," Acta Neurochir. 140(10), 995-1000 (1998).

9. R. Weersink, M.S. Patterson, K. Diamond, S. Silver, N. Padgett. "Noninvasive measurement of fluorophore concentration in turbid media with a simple fluorescence/reflectance ratio technique," Appl. Opt. 40(34): 6389-6395 (2001).

10. J. Wu, M.S. Feld, R.P. Rava. "Analytical model for extracting quantitative fluorescence in turbid media," Appl. Opt. 32, 3585-3595 (1993).

The invention claimed is:

1. A method for quantifying an absolute concentration of fluorophore in a target turbid medium, the method comprising:

detecting fluorescence emission from a target surface of the target turbid medium, the detected fluorescence emission including fluorescence emission of the fluorophore generated using a fluorescence excitation wavelength provided to the target turbid medium;

detecting diffuse reflectance over a spectral range of wavelengths from the target surface at at least two different predetermined distances from one or more broadband excitation sources to obtain two respective diffuse reflectance spectra;

determining an absorption coefficient ($\mu_a$) and a transport scattering coefficient ($\mu'_s$) of the target turbid medium using the two respective diffuse reflectance spectra and a priori absorption and transport scattering spectra of a known turbid medium; and determining the absolute concentration of the fluorophore in the target turbid medium using the detected fluorescence emission and the determined absorption and transport scattering coefficients;

wherein determining the absorption coefficient ($\mu_a$) and transport scattering coefficient ($\mu'_s$) comprises:

receiving an a priori absorption coefficient spectrum ($\mu_a(\lambda)$) and an a priori transport scattering coefficient spectrum ($\mu'_s(\lambda)$) as functions of wavelength, and calculating the absorption coefficient ($\mu_a$) and the transport scattering coefficient ($\mu'_s$) in absolute units for the fluorescence excitation wavelength based on the a priori absorption and transport scattering coefficient spectra and detected diffuse reflectance over the spectral range of wavelengths at the two predetermined distances;

wherein the detected fluorescence emission comprises a detected fluorescence spectrum, the method comprising calculating a quantitative fluorescence spectrum in absolute units from the detected fluorescence spectrum using the determined absorption and transport scattering coefficients of the target turbid medium; wherein the two respective diffuse reflectance spectra each include a separate and distinct spectral range where the absorption and transport scattering coefficients can be measured, the spectral range of one of the two respective diffuse reflectance spectra overlapping with a portion of the spectral range of the other of the two respective diffuse reflectance spectra to extend the dynamic range of optical properties of any one of the two respective diffuse reflectance spectra.

2. The method of claim 1 wherein the target turbid medium is biological tissue.

3. The method of claim 1, wherein the fluorescence emission is detected at a distance from a fluorescence excitation source that is equal to one of the at least two different predetermined distances.

4. The method of claim 1, wherein the absorption coefficient spectrum and the transport scattering coefficient spectrum are detected over the spectral range of wavelengths.

5. The method of claim 1, wherein the detected fluorescence spectrum comprises background autofluorescence emission of the target turbid medium.

6. The method of claim 1, wherein determining the absolute concentration of the fluorophore in the target turbid medium comprises decomposing the quantitative fluorescence spectrum into fluorescence emission of the fluorophore and background autofluorescence emission of the target turbid medium.

7. The method of claim 1, wherein determining the absolute concentration of the fluorophore is based on a known fluorescence quantum yield of the fluorophore and a known absorption coefficient of the fluorophore at the fluorescence excitation wavelength and a known fluorescence emission spectrum of the fluorophore.

8. The method of claim 1, wherein the at least two different predetermined distances are predetermined based on a desired range of absorption and transport scattering properties of the known turbid medium.

9. The method of claim 1, wherein the a priori absorption and transport scattering spectra of a known turbid medium includes general shapes of the absorption and transport scattering spectra of the known turbid medium.

10. The method of claim 1, wherein determining the absolute concentration of the fluorophore comprises spectral decomposition of the quantitative fluorescence spectrum in absolute units to remove background autofluorescence of the target turbid medium from the absolute concentration of the fluorophore.

11. The method of claim 1 comprising determining the absolute concentration of the fluorophore based on the detected fluorescence emission, the two diffuse reflectance spectra, the determined absorption and transport scattering coefficients, and the a priori absorption and transport scattering spectra of the known turbid medium, wherein the a priori absorption and transport scattering spectra of the known turbid medium constrains the determination of the determined absorption and transport scattering coefficients.

12. The method of claim 11 further comprising calibrating a detector using a phantom to provide a reference fluorescence measurement for calculating the quantity of fluorescence.

13. The method of claim 1, wherein the spectral range of wavelengths used to generate the diffuse reflectance spectra ranges from visible to near infrared light.

14. The method of claim 13, wherein the spectral range of wavelengths ranges from 450 to 850 nm.

15. The method of claim 1, wherein the quantitative fluorescence spectrum in absolute units ($f_{x,m}$) is based on the product of a fluorescence quantum yield ($Q_{x,m}$) and the absorption coefficient at the fluorescence excitation wavelength ($\mu_{af,x}$).

16. The method of claim 15, wherein the quantitative fluorescence spectrum is defined by equation (5):

$$f_{x,m} = Q_{x,m}\mu_{af,x} = \left(\frac{\mu_{a,x}}{1-R_{t,x}}\right)\left(\frac{F_{x,m}}{R_m}\right), \quad (5)$$

where:
- $\mu_{a,x}$ is the total absorption,
- $R_{t,x}$ is the total diffuse reflectance,
- $F_{x,m}$ is the measured fluorescence, and
- $R_m$ is the measured diffuse reflectance.

17. The method of claim 1, wherein the a priori absorption coefficient spectrum ($\mu_a(\lambda)$) is based on the absorption coefficients of oxyhemoglobin and deoxyhemoglobin.

18. The method of claim 17, wherein the a priori absorption coefficient spectrum ($\mu_a(\lambda)$) is defined by equation (9):

$$\mu_a(\lambda)=c_{Hb}[StO_2\mu_a^{oxyHb}(\lambda)+(1-StO_2)\mu_a^{deoxyHb}(\lambda)], \quad (9)$$

where:
- $c_{Hb}$ is a total hemoglobin concentration,
- $\mu_a^{oxyHb}(\lambda)$ is an absorption coefficient of oxyhemoglobin as a function of wavelength,
- $\mu_a^{deoxyHb}(\lambda)$ is an absorption coefficient of deoxyhemoglobin as a function of wavelength,
- $StO_2$ is an oxygenation fraction, and
- $\lambda$ is wavelength.

19. The method of claim 18, wherein the a priori transport scattering coefficient spectrum ($\mu'_s(\lambda)$) is defined by equation (10):

$$\mu_s'(\lambda)=A\lambda^{-b} \quad (10)$$

wherein:
- A and b are constants, and
- $\lambda$ is wavelength.

20. The method of claim 19, wherein the determined absorption and transport scattering coefficients are calculated using equation (11):

$$R(\lambda) = \frac{a'}{4\pi}\left[z_0\left(\mu_{\mathit{eff}}+\frac{1}{\rho_1}\right)\frac{\exp(-\mu_{\mathit{eff}}\rho_1)}{\rho_1^2}+ \right. \quad (11)$$
$$\left. (z_0+2z_b)\left(\mu_{\mathit{eff}}+\frac{1}{\rho_2}\right)\frac{\exp(-\mu_{\mathit{eff}}\rho_2)}{\rho_2^2}\right],$$

wherein:
- $R(\lambda)$ is diffuse reflectance as a function of wavelength,
- $a'$ is an reduced albedo,
- $z_0$ is $1/\mu'_s$
- $\mu_{\mathit{eff}}$ is $[3\mu_a(\lambda)\mu'_s(\lambda)]^{1/2}$
- $\rho_1$ is $z_0^2+r^2$
- $\rho_2$ is $(z_0^2+2zb)^2+r^2$
- r is distance from the one or more broad excitation sources at which diffuse reflectance is detected,
- $z_b$ is $2\kappa(3\mu'_s)^{-1}$
- $\kappa$ is an internal reflection parameter, and
- $\lambda$ is wavelength.

21. The method of claim 20, wherein $z_0$, $\rho_1$, $\rho_2$, $z_b$, and $\mu_{\mathit{eff}}$ are wavelength dependent.

22. A system for quantifying an absolute concentration of fluorophore in target tissue, the system comprising:
  a probe configured to:
    provide a fluorescence excitation wavelength and broadband wavelengths to the target tissue;
    detect fluorescence emission from a target surface of the target tissue, the detected fluorescence emission including fluorescence emission from the fluorophore; and
    detect the diffuse reflectance over a spectral range of wavelengths from the target surface at at least two different predetermined distances from one or more broadband excitation sources to obtain two respective diffuse reflectance spectra;
  a spectrometer for measuring the detected fluorescence emission and diffuse reflectance; and
  a processing device configured to:
    determine an absorption coefficient ($\mu_a$) and a transport scattering coefficient ($\mu'_s$) of the target tissue using the two respective diffuse reflectance spectra and a priori absorption and transport scattering spectra of a known tissue; and
    determine the absolute concentration of the fluorophore in the target tissue based on the detected fluorescence emission and the absorption and transport scattering coefficients;
  wherein the processing device is configured to determine the absorption coefficient ($\mu_a$) and transport scattering coefficient ($\mu'_s$) by:
    receiving an a priori absorption coefficient spectrum ($\mu_a(\lambda)$) and an a priori transport scattering coefficient spectrum ($\mu'_s(\lambda)$) as functions of wavelength, and calculating the absorption coefficient ($\mu_a$) and the transport scattering coefficient ($\mu'_s$) in absolute units for the fluorescence excitation wavelength based on the a priori absorption and transport scattering coefficient spectra and detected diffuse reflectance over the spectral range of wavelengths at the two predetermined distances;

wherein the detected fluorescence emission comprises a detected fluorescence spectrum, and the processing device is configured to:

calculate a quantitative fluorescence spectrum in absolute units from the detected fluorescence spectrum using the determined absorption and transport scattering coefficients of the target tissue; wherein the two respective diffuse reflectance spectra each include a separate and distinct spectral range where the absorption and transport scattering coefficients can be measured, the spectral range of one of the two respective diffuse reflectance spectra overlapping with a portion of the spectral range of the other of the two respective diffuse reflectance spectra to extend the dynamic range of optical properties of any one of the two respective diffuse reflectance spectra.

23. The system of claim 22, wherein the at least two different predetermined distances are predetermined based on a desired range of absorption and transport scattering properties of the known tissue.

24. The system of claim 22, wherein the a priori absorption and transport scattering spectra of a known turbid medium includes general shapes of the absorption and transport scattering spectra of the known tissue.

* * * * *